(12) United States Patent
Hugo

(10) Patent No.: US 6,254,393 B1
(45) Date of Patent: Jul. 3, 2001

(54) SYSTEM FOR REMOVING A DEFECT IN A TOOTH AND INSERT OR TOOL FOR SUCH A SYSTEM

(75) Inventor: Burkhard Hugo, Hettstadt (DE)

(73) Assignee: Kaltenbach & Voigt GmbH, Biberach (DE)

( * ) Notice: Subject to any disclaimer, the term of this patent is extended or adjusted under 35 U.S.C. 154(b) by 0 days.

(21) Appl. No.: 09/200,862

(22) Filed: Nov. 27, 1998

Related U.S. Application Data

(62) Division of application No. 08/669,344, filed on Jul. 2, 1996, now Pat. No. 6,022,217.

(30) Foreign Application Priority Data

Nov. 4, 1994 (DE) .................................. 44 39 410

(51) Int. Cl.[7] .................................................. A61C 5/04
(52) U.S. Cl. .................................................. 433/226
(58) Field of Search .................. 433/226, 215, 433/119

(56) References Cited

U.S. PATENT DOCUMENTS

| | | | |
|---|---|---|---|
| 2,924,013 | * | 2/1960 | Wowra .................. 433/116 |
| 3,241,239 | * | 3/1966 | Ellis ..................... 433/166 |
| 3,924,335 | * | 12/1975 | Balamuth et al. ......... 433/119 |
| 4,353,696 | * | 10/1982 | Bridges ................. 433/166 |
| 4,526,541 | * | 7/1985 | Hubschmid ............. 433/165 |
| 4,666,405 | * | 5/1987 | Ericson ................. 433/229 |
| 4,696,646 | * | 9/1987 | Maitland ............... 433/229 |
| 4,726,770 | * | 2/1988 | Kurer .................. 433/229 |
| 4,971,558 | * | 11/1990 | Jacobi ................. 433/226 |
| 4,993,951 | * | 2/1991 | Schumacher ........... 433/226 |
| 5,098,300 | * | 3/1992 | Zaki .................... 433/226 |
| 5,358,406 | * | 10/1994 | Bjerknes ............... 433/226 |
| 5,489,208 | * | 2/1996 | Mandell ................ 433/165 |
| 5,505,617 | * | 4/1996 | Skeppmark et al. ..... 433/165 |
| 5,531,722 | * | 7/1996 | Van Hale .............. 433/116 |
| 5,567,156 | * | 10/1996 | Hagne et al. .......... 433/226 |
| 5,695,340 | * | 12/1997 | Lee et al. ............. 433/226 |

FOREIGN PATENT DOCUMENTS

| | | | |
|---|---|---|---|
| 1 258 017 | 1/1968 | (DE) . | |
| 4209191 A1 | 5/1993 | (DE) . | |
| 295 03 782 U | 4/1995 | (DE) . | |
| 0 039 300 | 11/1981 | (FR) . | |
| 830 142 | 3/1960 | (GB) . | |
| 830142 | * | 3/1960 | (GB) ..................... 433/165 |

* cited by examiner

*Primary Examiner*—John J. Wilson
(74) *Attorney, Agent, or Firm*—Fitzpatrick, Cella, Harper & Scinto

(57) ABSTRACT

System for the removal of a defect in a tooth (71), consisting of an oscillatingly movable tool (3) having working surfaces (56) for an abrasive making of a cavity (K) in the tooth, a filling material for filing the cavity (K), an insert (91, 91A) which can be placed into the cavity (K), which with regard to its surface region surrounded by the cross-sectional walls (KW) of the cavity (K) is pre-fabricated adapted to the dimension and shape, and a binding material (92), which hardens or cures, for bonding the insert (91, 91A) with the walls (KW) of the cavity (K).

17 Claims, 13 Drawing Sheets

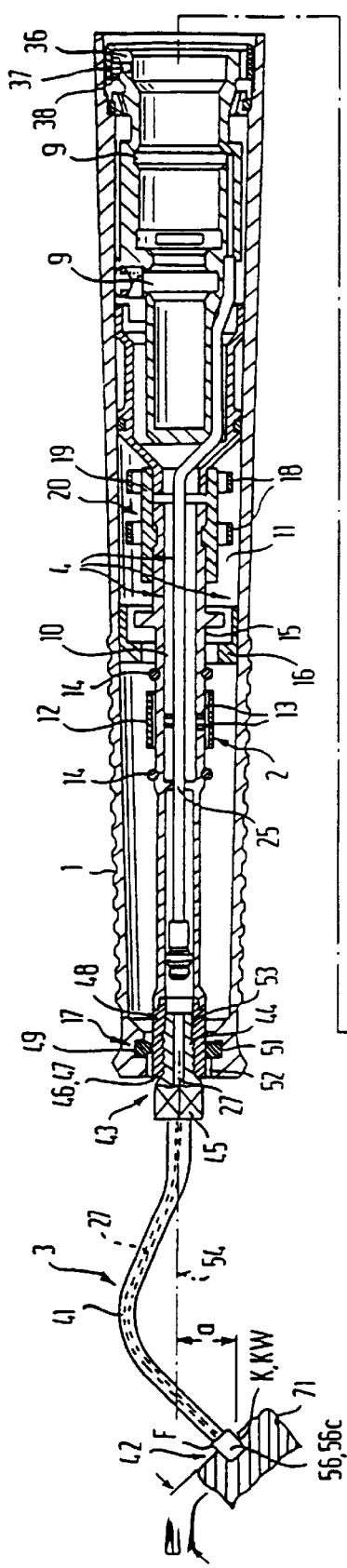

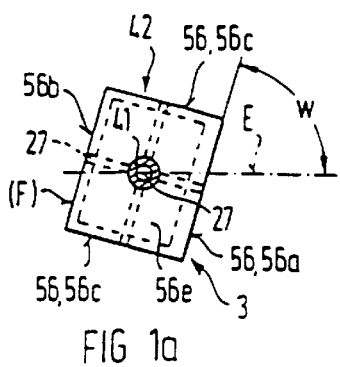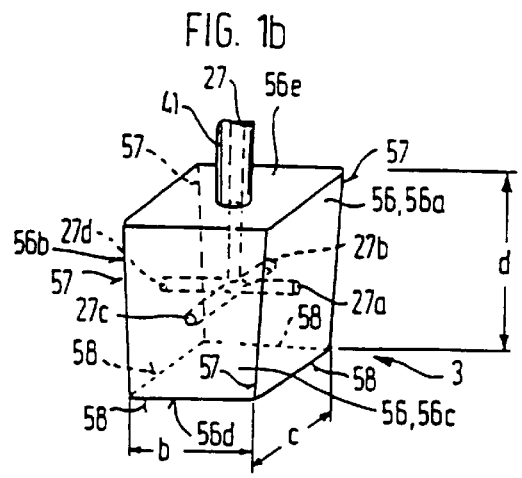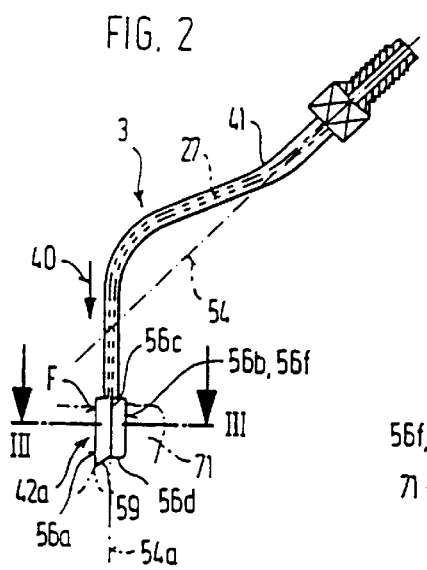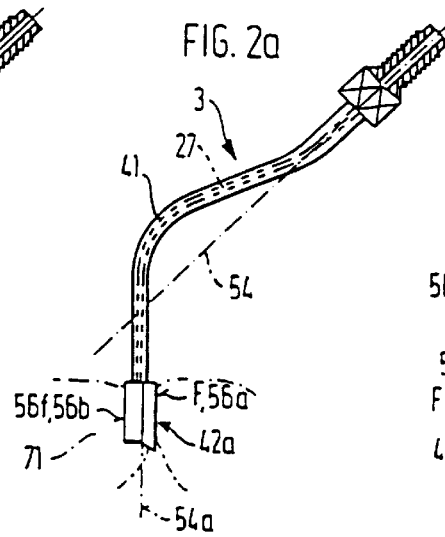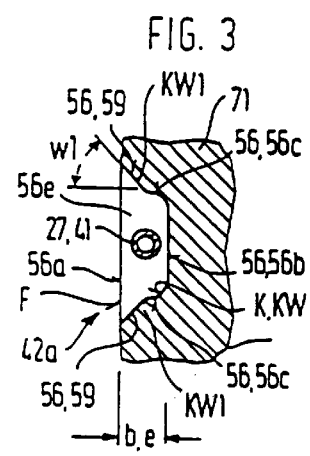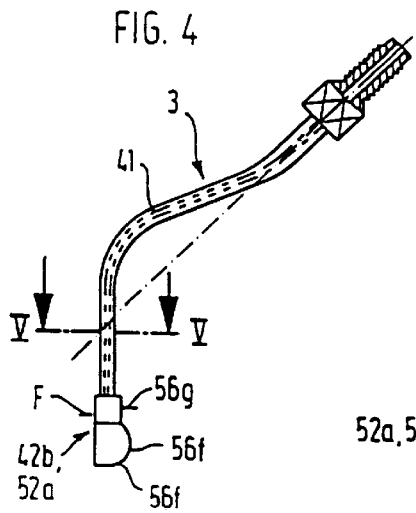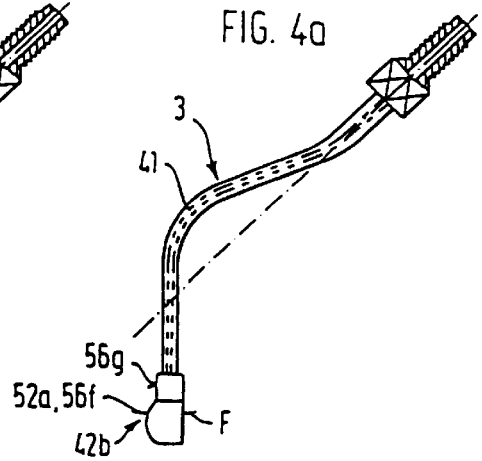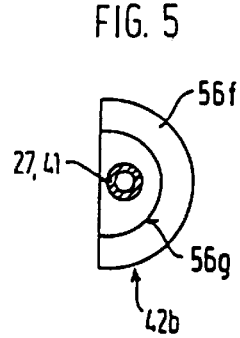

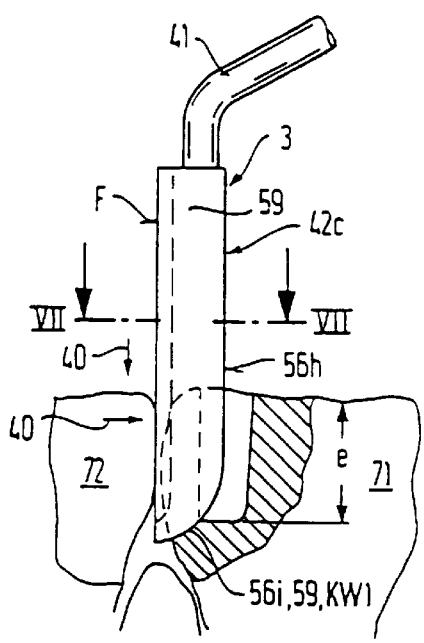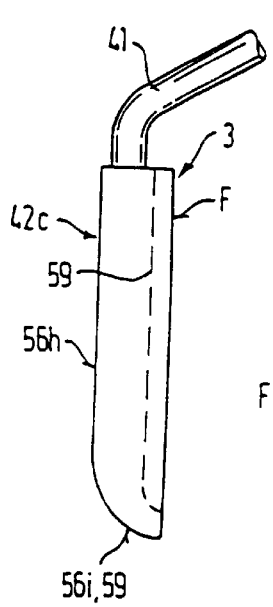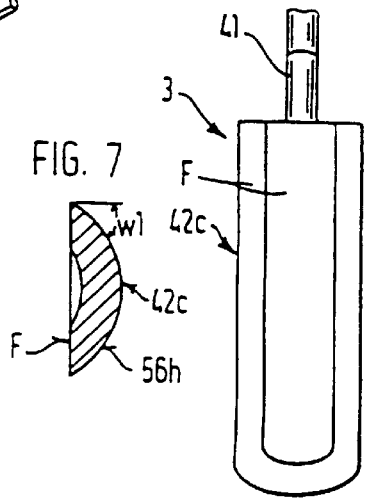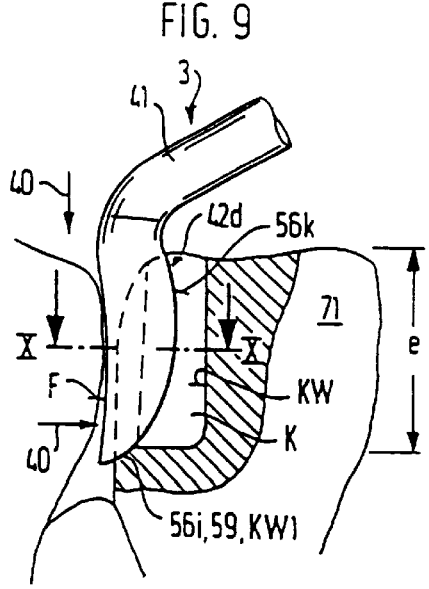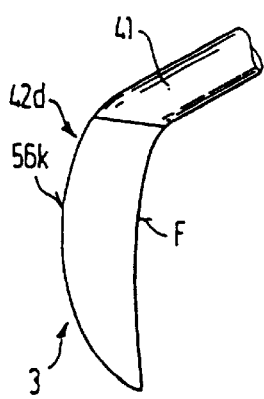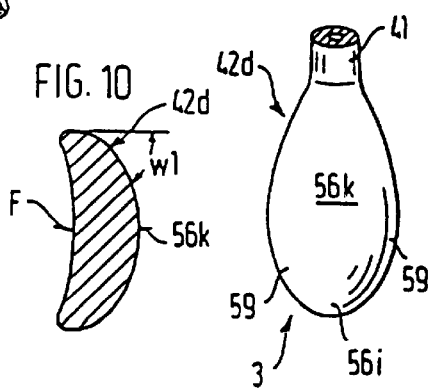

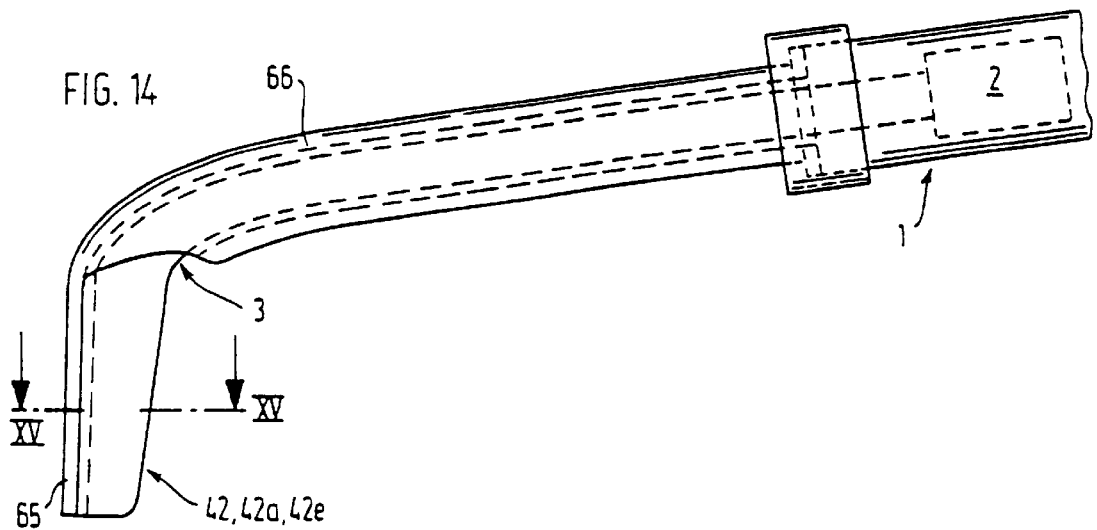
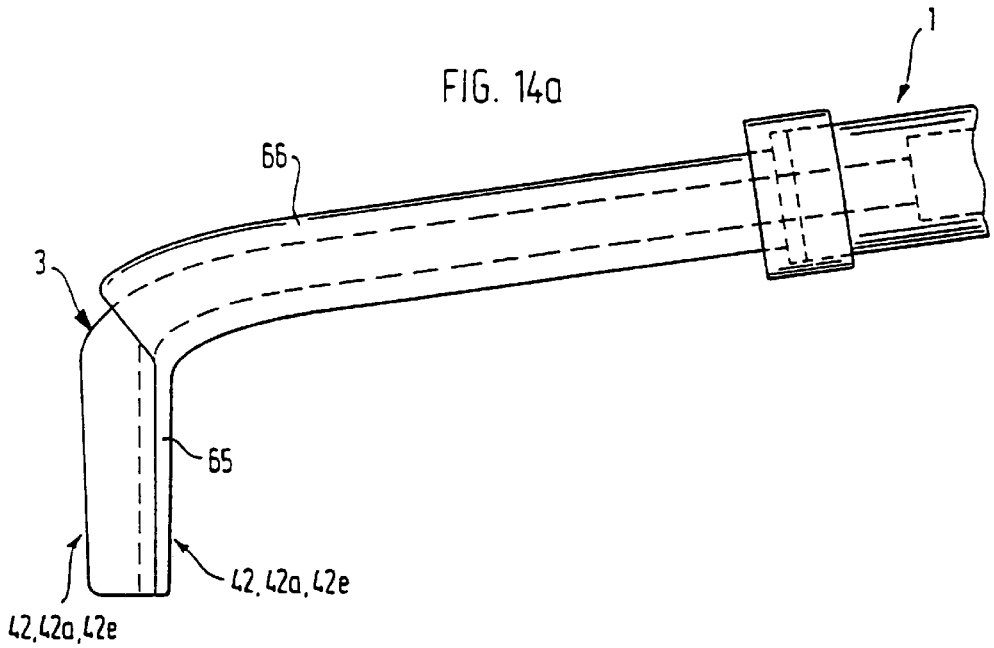
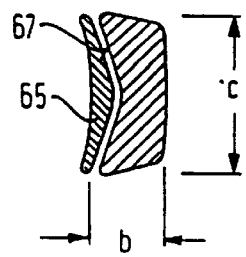

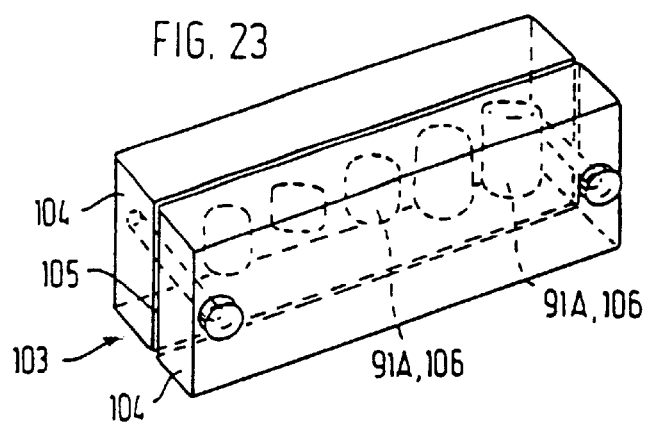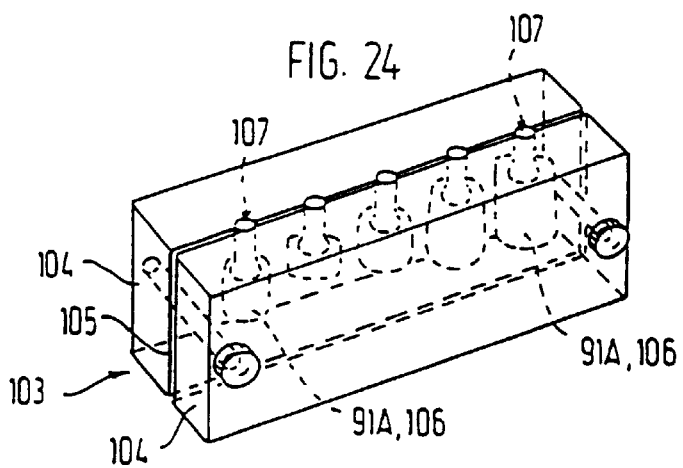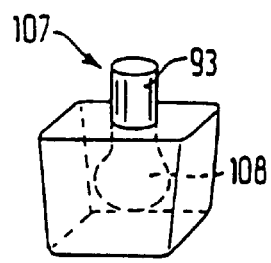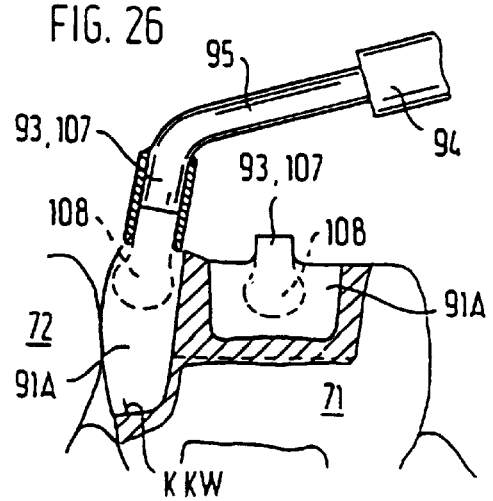

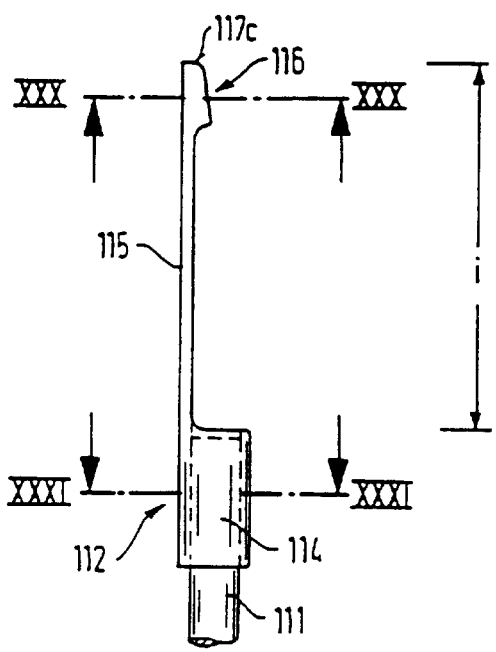
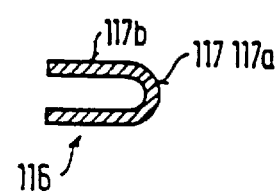
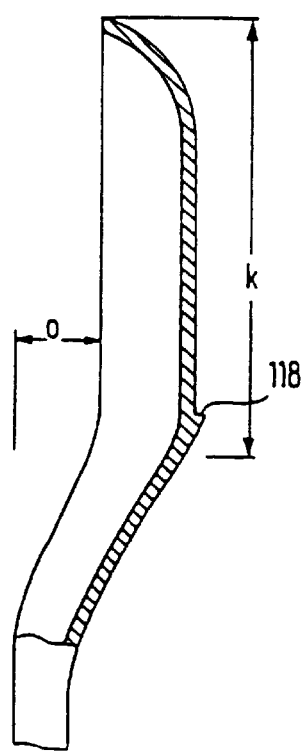
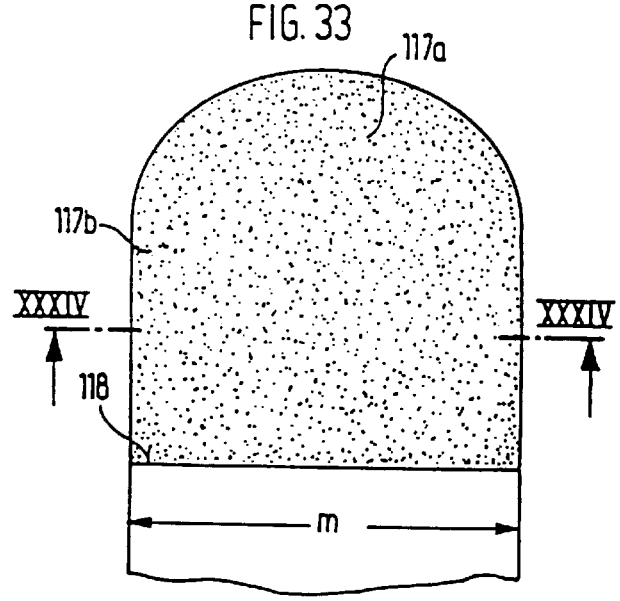

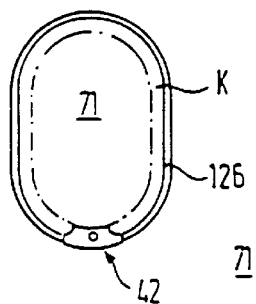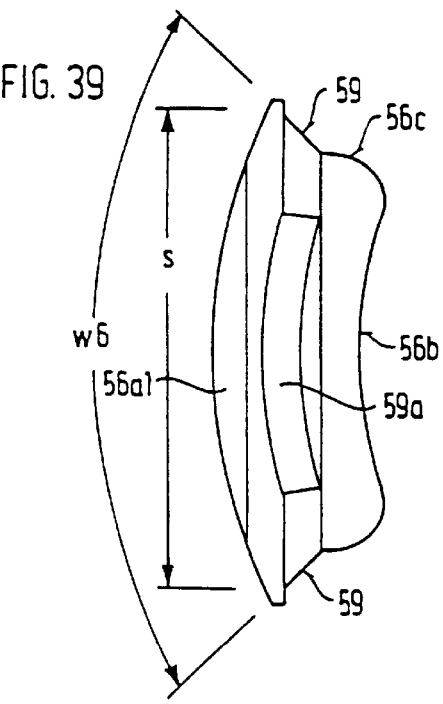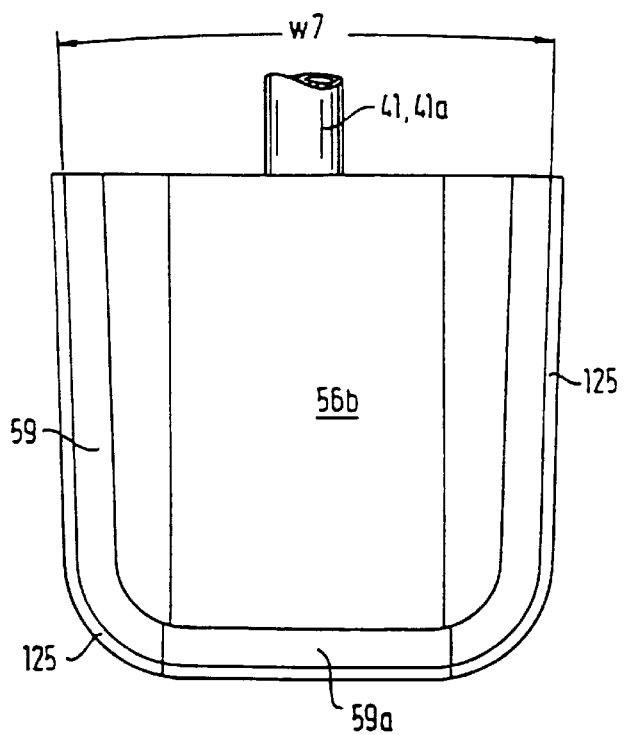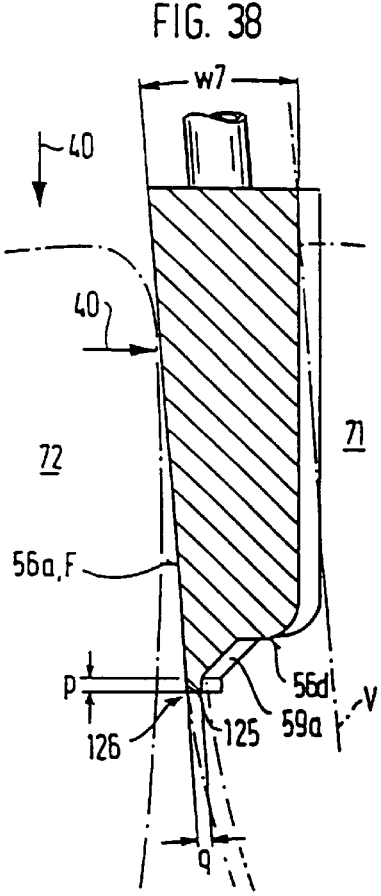

SYSTEM FOR REMOVING A DEFECT IN A TOOTH AND INSERT OR TOOL FOR SUCH A SYSTEM

CROSS REFERENCE TO RELATED APPLICATIONS

This is a division of application Ser. No. 08/669,344 filed Jul. 2, 1996, now U.S. Pat. No. 6,022,217.

BACKGROUND OF THE INVENTION

1. Field of the Invention

The invention relates to a system or a tool or an insert for the removal of a defect in a tooth or for making a cavity in a tooth.

There are various causes which justify the making, by machining involving the removal of material, of a cavity in a tooth and the repair of the tooth by means of a treatment of the cavity. Such a measure may be effected e.g. for aesthetic reasons to remove an unsatisfactory form of a part of the tooth. In most cases, however, these measures are carried out for repairing an unhealthy tooth, namely for removing a carious defect. A further reason for a measure as described above can also be the exchange of tooth fillings which are unsatisfactory for a variety of reason.

2. Description of the Related Art

In DE 42 09 191 A1 there are described a device and a process for the treatment of natural hard tissue with the employment of oscillating tools. With this known device, to make an occlusal cavity, a tool is used which has at its surface geometrically defined cutting edges or has cutting edges of non-defined geometric form such as adherent diamond grains, which make possible working of the material of the tooth, with the removal of material, with the oscillating movement of the tool. With the tool, there is made a cavity having an inwardly converging peripheral wall the cross-sectional size of which is a multiple of the cross-sectional size of the tool and the cross-sectional form of which differs substantially from the cross-sectional form of the tool. The tool is held releasably in a handpiece by means of a mounting device. The tool has a fluid outlet, at a spacing to the rear from the handpiece head which receives the tool, through which outlet a flow of fluid, e.g. water or a saline solution, can be directed at the treatment site and onto the tool for the purpose of cooling and rinsing. Measures for filling the cavity and treating the tooth are not described in this document. This known device and this known process are not only work and time consuming so far as the preparation of the cavity is concerned but also with regard to the usual methods of filling the cavity, whereby in this respect demands are made on the practicability of the preparation work and treatment work, on the thereby necessary manipulability, on the firmness and load bearing and on the lifetime of the treatment.

The above described treatment measures in a tooth occur not only in its occlusal region but also in its lateral and approximal region. In particular approximal preparations and treatments are difficult to carry out because of a neighbouring tooth and the thus resulting restricted accessibility, whereby there is a danger of damage to the neighbouring tooth.

The treatment of a cavity with a laboratory-prepared inlay is work-intensive and correspondingly expensive. Further, the tooth to be treated can be definitively treated only in a second treatment session and thus with "double time". To reduce the outlay involved in a treatment, it has already been proposed to use inlays manufactured at the place of treatment, as is e.g. possible with the so-called computer controlled milling of inlays. Further, it has already been proposed to use for the treatment of cavities prefabricated inlays, whereby likewise a treatment in only one treatment session and thus at a "single time" is possible. With such a measure, however, special preparation and treatment measures are needed which are again time consuming and involve complicated manipulation and are expensive.

The object of the invention is to improve a system, an insert or a tool for removing a defect in a tooth.

According to one aspect of the invention, there is provided a material removing tool for working on a tooth to make a tooth cavity by oscillating movement, such tool comprising a shaft and an abrasive treatment section and characterized in that the abrasive section is formed by a working head having an abrasive working surface and an opposing smooth surface.

According to another aspect of the invention, there is provided novel insert for filling a cavity on a tooth which has been worked using an oscillatingly moveable tool, wherein the body of the insert is pre-fabricated so that its surface area enclosed by the cross-sectional walls of the cavity of its entire cross-sectional area is adapted to the cross-sectional dimension and shape of the tool and comprises bearing surfaces for abutting diverging edge surfaces on the cavity.

With the system in accordance with the invention there are employed a tool working in an oscillating manner for the preparation of a cavity, and an insert which can be inserted into the cavity, which are matched one to the other at least in the region which is defined by the tooth wall of the cavity surrounding the insert. By these means it is possible to prepare an exactly matched cavity and to treat the tooth without needing to direct special attention the matching form of the cavity and the insert. This is provided in that a tool working in an oscillating manner is used which, because of the oscillation, is independent of a rotational movement and thus can be manufactured in selected forms. With all these forms there can be produced in the tooth, in a simple manner, by machining involving the removal of material, a cavity corresponding to the form of the tool. The tool need only be sunk, oscillating, into the tooth material. Thereby a particular form for the cavity is automatically achieved. Thus, in that in accordance with the invention an insert is employed which is matched to the form and size of the tool at least in the region formed by the walls of the cavity, no special measures are needed for matching the form of the cavity to the insert, since agreement is reached automatically. The term agreement is to be understood in the sense that the form and size of the insert, taking into account a small amount of play or a small gap, correspond to the related form and size of the tool or of the cavity. Such an amount of play can be provided as a small difference in size or this amount of play can be provided automatically because of the oscillating movement of the tool. Such an amount of play is necessary in order to be able to place the insert into the cavity without jamming. Thereby, it is to be taken into the consideration that because of the roughness of the wall surfaces of the cavity a certain amount of play is of advantage. Further, the amount of play or the gap is needed to be able to place therein plastic and curing or hardening bonding material and to ensure on the one hand a firm and on the other hand a sealed bond between the tooth and the insert.

The invention thus makes possible a simple, readily manipulable treatment of a tooth that can be rapidly carried out, which is not only economical but also of particular quality with regard to its firmness and load bearing and lifetime.

The system in accordance with the invention is suitable particularly advantageously for a treatment in the inaccessible approximal region of the teeth. Thereby, damage to the neighbouring teeth can be avoided since those surfaces of the tool which in the course of preparation come into contact with the neighbouring tooth surface are not configured for removing material.

The surfaces of the tool and the associated insert which do not belong to the region which is defined by means of the wall surfaces of the cavity need not to be adapted one to the other in the above-described sense. When such a region surface is a lateral or approximal surface of the insert this can likewise be pre-fabricated e.g. in an idealized form. In the occlusal region of a purely occlusal or also lateral or approximal cavity, the insert may be larger than is necessary and after attachment in the cavity may be adapted through machining involving removal of material. This is naturally true also for a lateral surface of the insert. Within the scope of the invention it is however also possible to provide the vertical dimension for an occlusally open cavity smaller than the necessary dimension and after attachment of the insert in the cavity to complete this dimension by means of a building up of material, e.g. at the same time as a region extending to a neighbouring or to the other occlusal region of the tooth.

It is advantageous to provide at a treatment station a plurality of tools and a plurality of mold parts adapted thereto in the sense in accordance with the invention, which with regard to their size in one and/or both dimensions, their cross-sectional form and/or their height and/or their coloring are different. By these means it is not only possible to use for a particular size of the defect a correspondingly dimensioned tool and also an associated insert, but it is also possible to make a cavity through the use one after another of progressively larger tools in a plurality of working steps.

A further advantage of the invention consists in forming mutually oppositely lying surfaces of the tool convergingly in the forward driving direction of the tool so that the tool worked into the tooth material can be withdrawn from the thus formed cavity without jamming.

Further, the invention relates also to a tool and an insert having the features in accordance with the invention. The above described advantages apply also to the tool and the insert part.

The invention relates also to a process for removal of a defect in a tooth which is advantageous for the same or corresponding reasons.

BRIEF DESCRIPTION OF THE DRAWINGS

Below, the invention and further advantages which can be achieved thereby will be described in more detail with reference to advantageous embodiments and to the drawings, which show:

FIG. 1 a tool in accordance with the invention, in a side view, with an associated handpiece for the attachment and manipulation of the tool, in axial section;

FIG. 1a working head of the tool in a view from above;

FIG. 1b the working head in a perspective representation;

FIG. 1c a working head of the tool in a side view;

FIG. 2 the tool in a modified configuration;

FIG. 2a a tool in accordance with FIG. 2 in a further modified configuration;

FIG. 3 the section III—III in FIG. 2;

FIG. 4 a tool in a further modified configuration;

FIG. 4a the tool according to FIG. 4 in a further modified configuration;

FIG. 5 the section V—V in FIG. 4;

FIG. 6 tool in a further modified configuration;

FIG. 6a the tool according to FIG. 6 in a further modified configuration;

FIG. 7 the section VII—VII in FIG. 6;

FIG. 8 the tool according to FIG. 6 in a side view from the left;

FIG. 9 a tool in a further modified configuration;

FIG. 9a the tool according to FIG. 9 in a further modified configuration;

FIG. 10 the section X—X in FIG. 9;

FIG. 11 the tool according to FIG. 9 in a side view from the left;

FIG. 14 a tool with a handpiece in a modified configuration;

FIG. 14a the tool according to FIG. 14 in a modified configuration;

FIG. 15 the section XV—XV in FIG. 14;

FIG. 23 a press or mold form for a plurality of inserts, in a perspective representation;

FIG. 24 an insert, in perspective representation, in a modified configuration;

FIG. 25 a press or mold form for an insert in accordance with FIG. 24, in a perspective representation;

FIG. 26 a tooth with an approximal insert and an occlusal insert, partially sectioned;

FIG. 29 a tool in a further modified configuration, in a side view;

FIG. 30 the partial section XXX—XXX of FIG. 29;

FIG. 31 the partial section XXXI—XXXI of FIG. 29;

FIG. 32 a longitudinal section through a tool in a further modified configuration;

FIG. 33 a working head according to FIG. 32, in a side view from the right;

FIG. 34 the section XXXIV—XXXIV in FIG. 33;

FIG. 37 a working head in a view from the front, in a further modified configuration;

FIG. 38 the working head according to FIG. 37 in lateral section;

FIG. 39 the working head in a view from below;

FIG. 40 a tooth with a working head according to FIG. 37, in a view from above.

DETAILED DESCRIPTION OF THE PREFERRED EMBODIMENTS

Figure 12:
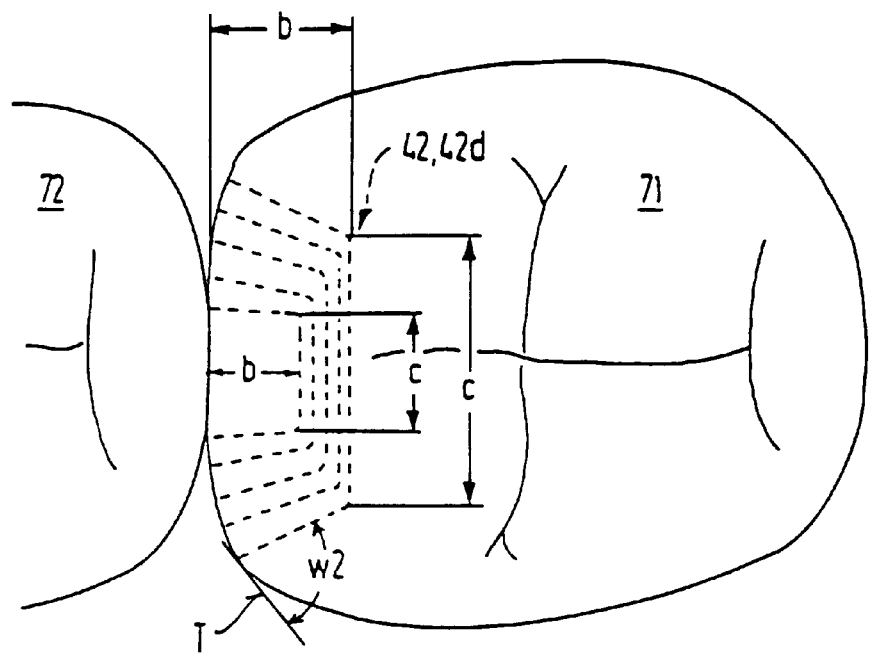
FIG. 12 a tooth, in a view from above, with a plurality of schematically indicated working heads of different sizes.

The handpiece consists of an elongate round grip sleeve 1 in which there is arranged an oscillation generator 2—which is preferably releasably connected with the tool 3—for bringing the tool 3—mounted at the forward end of the grip sleeve 1 so that it is able to oscillate—into oscillation and thereby to transmit oscillation to the tool 3. The grip sleeve 1 has, in its interior, two treatment medium lines 4 which extend from the rear forwardly. Via connection lines 7 of a connection piece 5 arranged at the end of the grip sleeve 1 away from the tool, these medium lines 4 are connected to respective connection lines 6 leading to a medium source which is not illustrated, which connection lines extend in a flexible supply hose with which the connection piece 5 is connected.

The connection piece 5 is formed as a quick-release and quick-assembly rapid-action coupling which is freely rotatable relative to the grip sleeve 1. The rapid-action coupling and the end of the grip sleeve 1 away from the tool are provided with medium transfer means 8, 9 which are functional in any rotational position, whereby cooling medium exit opening of one of the connection lines 6 and 9 is a cooling medium supply channel of a cooling medium line 25 leading to the tool 3.

As a further medium line 4, there is provided an energy supply line extending to the oscillation generator 2.

As an additional medium line 4 there is provided the cooling medium line 25 leading to the tooth de-scaling tool 3. The cooling medium may be air, water or a spray formed by means of an air-water mixture. The cooling medium line 25 opens into the tool 3 which is formed to be hollow, which has a cooling medium exit opening directed at the treatment zone or exit openings emerging at its working surfaces. The hollow channel of the tool 3 is indicated with 27.

The connection piece 5 is provided with a central guide pin 28, circular in cross-section, which can be inserted and latched into the end of the grip sleeve 1 away from the tool, relative to which guide pin the grip sleeve 1 is freely rotatable also in the latched-in condition.

In detail, the medium transfer means are formed each by exit openings 8 of the connection channels 7 connected to the connection lines 6, which exit openings surround the guide pin 28 and come into contact on the grip sleeve inner walls and are arranged on annular sealing elements 29, and are also formed by the ring channels provided in the region of the grip sleeve inner wall and associated with the exit openings 8.

The connection piece 5 has at least one control member 31, provided with a setting member 30 which is externally actuable, associated with at least the medium line 4 provided as cooling medium line 25.

Insofar as the elasticity of the sealing elements 29 is not sufficient to provided a clamping force which can bring about a latched-in retention of the guide pin 28 in the grip sleeve 1, there can be provided for this purpose, as represented, a special latch arrangement 39 which retains the guide pin 28 in the desired axial inserted position. For this purpose, there is arranged on the outer wall of the guide pin 28 a special latch ring channel 35 and there is arranged in the wall of the grip sleeve 1 at least one latch ball 37 mounted in a recess 36. The latch ball 37 thereby engages into the latch ring channel 35, under the effect of a spring 38, with the smaller part of its surface projecting beyond the inner surface of the wall of the grip sleeve 1. For this purpose, the recess 36 has a floor aligned with the above-mentioned inner surface of the wall of the grip sleeve 1, which floor has an opening which is smaller than the equatorial plane of the latch ball 37. During the insertion procedure or during the pulling apart procedure, the latch ball 37 is moved out of the latch ring channel 35 against the effect of the spring 38 so that upon the insertion procedure or the pulling apart procedure an easy and quick taking up and release of the latch-in position is provided.

The tool 3 consists of a shaft 41, a working head 42 at the forward end of the shaft 41 and a connection element 43 at the rearward end of the elongate shaft 41. With the present screw connection there is provided a threaded pin 44 which projects backwardly from a rotation engagement element 45, here a collar in the form of a hexagon. The rearward end of the rotation engagement element 45 is formed conically. With this outer conical surface 46, the tool 3, in the connected condition, abuts on a correspondingly formed internal conical surface 47 at the tool-side end of a bearing sleeve 48 which is connected in one piece or in two pieces with the sleeve-like resonating body 15 and is mounted in a bearing ring 49—which also forms the mounting 17—without play or with slight play for movement, which bearing ring 49 is attached to the grip sleeve 1 in the forward end region of the sleeve and may be formed by means of a ring of elastic material which sits in an internal groove 51 in the grip sleeve 1, whereby the bearing sleeve 48 penetrates the associated through-hole 52 in the grip sleeve 1 with radial spacing. In the mounting sleeve 48 there is arranged a coaxial bore having an internal thread 53, into which the threaded pin 44 can be screwed.

The shaft may extend straight or obliquely to the longitudinal middle axis of the preferably straight grip sleeve 1. In the present configuration, the shaft is a round rod the cross-sectional size of which continuously tapers down to the working head 42. Starting from the foot region of the shaft, the shaft 41 extends first obliquely to one side of the handpiece 1, and it is then bent towards the other side, whereby this shaft section 41a, extending in the oblique position preferably straight, extends beyond the longitudinal middle axis 54 so that the working head 42 is located at a spacing a from the longitudinal middle axis 54 in an oblique position on the other side. In the present configuration, the spacing a is about 5 mm.

The shaft may be formed by a tube which is placed in a corresponding hole in the rotational engagement element 45 and is connected therewith. The hollow channel 27 extending in the shaft 41 or the tube can open out in the region of the shaft in a position directed towards the working head 42. Preferably, the hollow channel 27 extends longitudinally through the shaft 41 up into the working head 42, as will be described below. The shaft 41 is preferably of high tensile springy material, preferably alloyed steel.

As can be understood from FIGS. 1a, 1b and 1c the working head 42 is a block-like body having a rear wall 56a, a forward wall 56b opposite thereto, and two mutually oppositely lying side walls 56c, a floor wall 56d and an upper wall 56e in the region of which, preferably in the middle, the working head 42 is nonreleasably connected with the shaft 41 preferably by means of soldering or welding. The cross-sectional size of the working head 42 tapers, preferably continuously, from the top downwardly. The circumferential walls, which are flat in the present exemplary embodiment, thereby enclose an angle with the associated vertical of about 2 to 8°, in particular about 4 to 6°, so that the mutually oppositely lying walls converge downwardly. The vertical edges 57 and the circumferential edges 58 of the floor wall 56c are preferably rounded.

For the use of the working head 42 in the middle occlusal region of a tooth, all wall surfaces 56a to 56d of the working head 42 are provided with a plurality of in particular point-like cutting edges which are arranged distributed over the associated surface and with oscillating drive provide for the preparation of a cavity in the tooth. Here, the cutting edges may be geometrically defined or undefined. Preferably, the working surfaces 56 are occupied by hard adherent grains preferably of diamond feldspar or ceramics, and are thus abrasive. There may also be other abrasive working surfaces 56 which upon oscillating movement provide a removal of the tooth material.

With a working head 42 set up in particular for the approximal region, the surface F towards the neighbouring tooth is formed to be smooth so that it cannot damage the neighbouring tooth and can form a free or support surface F for support on the neighbouring tooth.

Thereby, the smooth surface F may be one of the four lateral working surfaces 56. Preferably, the rear wall 56a or the front wall 56b forms the smooth support surface F. This is determined for reasons of manipulation and the geometrical position of the approximal tooth surface to be treated (directed to the rear or to the fore) in the mouth of the patient. For the same reason it is advantageous to arrange to working head 42 so turned or rotated that the rear surface 56a or the front surface 56b encloses an acute angle w of approximately 60 to 80°, in particular approximately 70 to 75°, with the associated vertical longitudinal plane E.

With the configuration of the working head 42 in accordance of FIG. 2, in which the same or similar parts are designated with the same reference signs, the working head 42a is, with regard to its dimension b transverse to the shaft 41 and extending in the longitudinal direction of its middle axis 54a, preferably smaller than its dimension c transverse to the shaft 42 and transverse to the middle axis 54a, so that it has approximately the form of small plate or tip. With this configuration, the rear surface 56a of this working head 42a is formed to be smooth whereby it can be flat or also—seen along the shaft 42—rounded in the shape of a section of a cylinder. This configuration is particularly well suited for an approximal preparation, which is already provided in that the dimension b is relatively small and in the present configuration is only about 1 to 2 mm, whilst the dimension c may be about 1.5 to 5 mm and the dimension d transverse to the middle axis 54a and extending longitudinally of the shaft 41 is about 3 to 6 mm. The working in or advancing direction 40 is approximately parallel to the axis of the tooth starting from its occlusal surface.

Preferably, with an exception at the upper wall 56e, in the edge region all three remaining peripheral edges of the rear surface 56a are arranged as divergent surfaces 59, in particular oblique surfaces or chamfers, on the side walls 56c and the floor wall 56d which can run out into the peripheral edges of the front surface 56b and as with the other working surfaces 56 are occupied by material removing cutting edges as particles. Thereby, the transitions between the rear wall 56a and the side walls 56c or the floor wall 56d, or between these, and the divergent surfaces 59, can be rounded. The front wall 56b can, with reference to the middle axis 54a, be parallel or somewhat downwardly convergently inclined. These divergent surfaces 59 generate in the associated peripheral region of the cavity K corresponding edge surfaces KW1 at the edge of the cavity walls KW. The angles w1 of the divergent surfaces 59 may be about 30 to 60° in particular about 45°.

There may be arranged divergent surfaces, comparable with the divergent surfaces 59, also in the region of the peripheral edges of the upper wall 56e on the working head 42, whereby in this occlusal region all four walls 56a, 56b, 56c are provided with corresponding divergent surfaces.

With the configuration according to FIGS. 4 and 5, in which the same or similar parts are likewise given the same reference signs, the working head 42b is provided with a convexly rounded forward and rearward working surface 56f, whereby this surfaces can be formed as section of a sphere or hemispherically. The front surface 56a, facing the neighbouring tooth, is on the other hand formed as a smooth free surface F. Such a configuration serves preferably for preparation of a small cavity K in particular in the approximal region of the tooth. In the transition region between the working head 42b and the shaft 41 there may be provided a tapered neck-shaped shaft transition having a forward working surface 56g which is arched convexly towards the rear side, e.g. in the form of a section of a cylinder, in particular half-cylindrically or half-conically. Such a working head 42b has approximately the form of a half pear.

With the working heads provided for an approximal preparation the smooth surface F, facing the neighbouring tooth, may be—seen longitudinally of and/or transversely of the shaft 41—lightly concavely rounded in the sense of a chamfer, whereby this concave rounding is adapted to the neighbouring tooth and is rounded corresponding to an average value.

Within the scope of the invention it is also possible to configure the working head flat such that it in substance has only divergent surfaces 59 and thus serves for the application of divergent edge surfaces KW1 to a cavity K which is already present. With smaller dimensioning of this form, the preparation of the smallest chamfer-like cavities is also possible, in particular in the space between teeth on the first treatment of carious defects. Such configurations are described in FIGS. 6 to 11. With the configuration according to FIGS. 6 to 8 there is provided a working head 42c in the form of a flat strip with parallel sides which at its free end may have a flat or rounded end face. The working surface 56a, which is at the rear side in the present configuration, is rounded in the shape of a section of a cylinder whereby this rounding transforms into a rounded or oblique end face at 56i. With this configuration, the working surfaces 56h, 56i form the divergent surfaces 59 whereby these divergent surfaces 59 may also be formed by means of oblique surfaces of striplike head 42c. When the free surface F is concavely rounded in the sense of a chamfer, see FIG. 7, then this chamfer ends before the free end of the working head 42c (see FIG. 8), so that the end face working surface 56i can be formed.

The configuration of the working head 42d in accordance with FIGS. 9 to 11 differs from that according to FIGS. 6 to 8 in that the form of the strip is not parallel but is formed with an egg shape as is shown by FIG. 11. Since this working head 42d is longitudinally rounded there is provided an ellipse-shape convex working surface 56k. As FIG. 9 shows by way of example it is also possible with all above-described exemplary embodiments to round the free surface F—seen in longitudinal and/or transverse direction—lightly concavely in accordance with an average amount.

The working surfaces 56f to 56k are abrasive through the presence of material-removing cutting edges or particles, e.g. are diamondised; have diamond applied thereto. The working surface 56k may also be formed as a smooth free surface. The edges may be rounded and not abrasive.

With the configurations according to FIG. 6 to 11, the dimension c may be so large that cavities K of different widths may be worked with one and the same working head 42c, 42d, whereby the diverging edge surfaces KW1 at the sides and at the floor of the cavity A can be worked in simultaneously. When the dimension c is smaller then the associated widths of the cavity K, then there is needed a lateral movement of the working head 42c, 42d in order to be able to work in the divergent edge surfaces KW1 one after another.

In all above-described configurations in accordance with FIGS. 2 to 11, the working surface 56 and the free surfaces F may face respectively in opposite directions, as is shown by FIGS. 1c, 2a, 4a and 6a. The arrangement in each case is dependent upon whether an approximal cavity K is to be prepared in the rearwardly facing or forwardly facing side of a tooth.

The working surfaces 56 to 56k are of corrosion resistant material, such as e.g. alloyed steel, whereby the working surfaces are provided with a diamond coating and are thus have diamondised.

Figure 13:
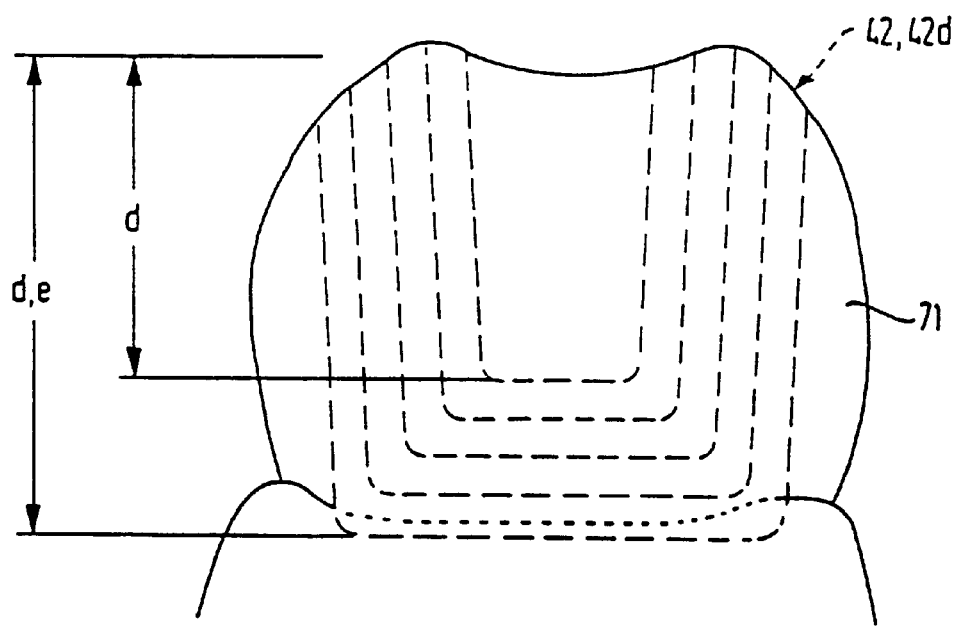
FIG. 13 the arrangement according to FIG. 12 in a side view from the left.

With all above-described exemplary embodiments it is advantageous to provide in each case a plurality of working heads of one basic form, of which the dimensions b and/or c and/or d differ in accordance with particular steps. Such a configuration is made more clear by FIGS. 12 and 13 which schematically show respective working heads 42 to 42d in five or more differing sizes. With a working head intended for an approximal preparation, with greater dimension c the divergence of the side surfaces 56c—approximately parallel to the occlusion surface—increases, so that the side surfaces—in the case of box type cavities—include an angle w2 of approximately 70 to 90° with a tooth tangent T.

Further, it is advantageous to provide for each particular size not only a single working head but a plurality, in particular two working heads 42 to 42d, of which one working head is intended for a rough pre-preparation and the other working head is intended for a fine or final preparation. In the case of a diamondisation, for a prepreparation this may be approximately 60 to approximately 80 μm, and for a fine preparation approximately 25 to 40 μm. The dimensioning of the pre-preparation instrument should be, with diamondisation applied, slightly smaller—in dependence upon the material removal properties—than the fine preparation instrument. Through the cavity provided by the pre-preparation, a defined sinking in of the fine preparation instrument, a fine removal of tooth material and a reproducible form and size of cavity is possible.

With the configuration according to FIGS. 14 to 15, in which the same and similar parts are likewise provided with the same reference signs, there is associated with the tool 3 or working head 42a—provided for an approximal preparation—a protection part 56 which is located on the side of the working head away from the working region, namely on the side directed towards the neighbouring tooth. With the present configuration, the protection part 65 is a narrow strip the width which is preferably so adapted to the dimension c of the working head that the side of the working head directed towards the neighbouring tooth is substantially completely covered by means of the protection part 65. The protection part 65 is rigidly connected with the grip sleeve 1 and thus does not take part in the oscillation movement. The protection part 65 may run as a protection strip from a pipe-like base part 66, that surrounds the shaft 41 at least partially with such a spacing that the shaft 41 and the working head do not contact the base part 66 and the protection part 65. In order to maintain the approximal dimension as small as possible it is advantageous to arrange the protection part 65 in a recess of the working head, at least partially sunk in. Such a configuration is shown in FIG. 15. This working head 42e has a triangular or trapezoidal recess 67 extending in its longitudinal direction, in which there extends a correspondingly formed protection strip 65 at a small spacing (gap) from the recess surface.

As is already the case with the configurations in accordance with FIGS. 1c, 2a, 4a and 6a, with this configuration also the working region of the working head and the protection part 65 may be arranged in oppositely directed arrangement, namely rotated or turned by approximately 180° or be arranged in another lateral arrangement, see FIG. 1a. The protection part 65 likewise consists of corrosion resistant material, in particular alloyed steel. The attachment to the grip sleeve 1 may be effected by means of a releasible or non-releasible connection, e.g. by means of a screw connection or by means of a retaining nut.

As further protection devices, hindering the damage of neighbouring tooth surfaces, there may serve partial coatings or "inlays" on the tool surfaces, the material properties of which such as e.g. the hardness or abrasivity do not damage tooth substance or repair materials, e.g. plastics such as teflon.

Figure 16:
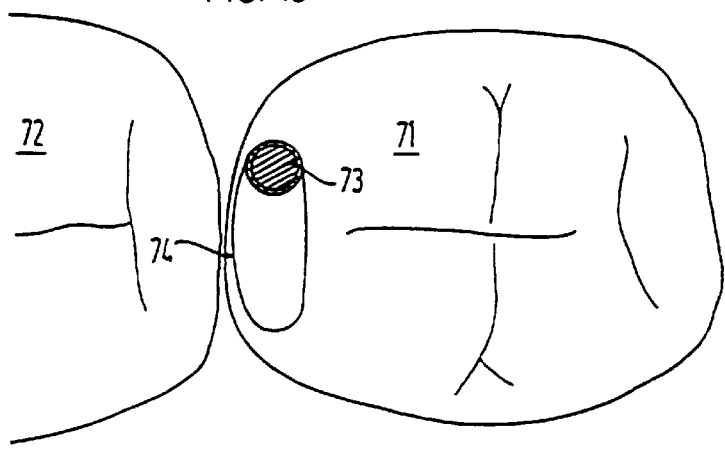
FIG. 16 a tooth, in a view from above, with a pre-prepared cavity.
Figure 17:
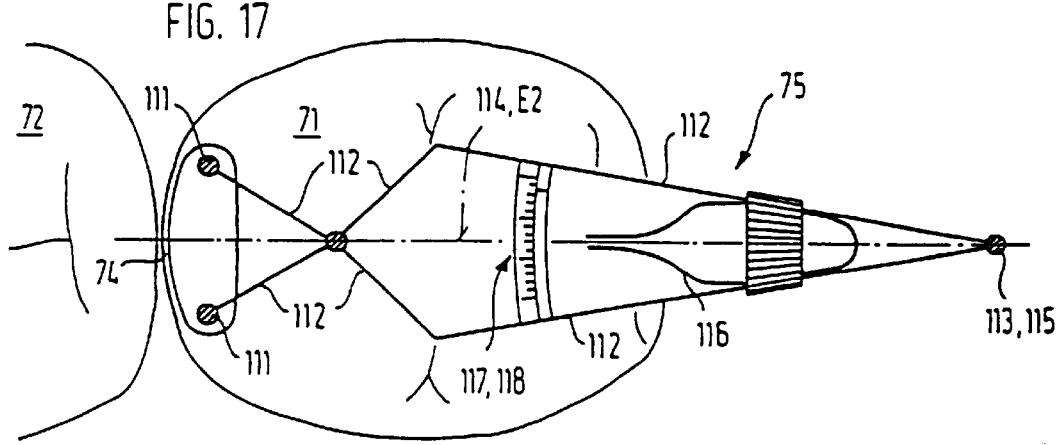
FIG. 17 the tooth according to FIG. 16 with a measuring tool for measurement of the cavity.

In the following, there will be described the treatment of a carious defect and/or a pre-existing repair of a tooth 21 in the approximal region, with reference to FIGS. 16 to 22. The carious defect and/or a pre-existing repair are removed by means of the preparation of the cavity K and moreover from the side of the occlusional region. This preparation may be effected with a working head 42a which, in the present case of a lower jaw tooth, is sunk in—with oscillating tool 3—from above. Thereby, the drive head 42a may be supported with its free surface F on the neighbouring tooth 72, without there being the danger of damage to the tooth 72, since only a slight frictional loading occurs. In place of the preparation with a working head 42a in accordance with the invention, a pre-preparation may be worked in with a conventional rotational tool 73 as shown by FIG. 16. As a precaution, when possible, this pre-preparation may be carried out except for a thin approximal remainder wall 74, in order not to damage the tooth 72. Then, this pre-preparation is measured with regard to its width, length and depth in order to be able to select the correct size for a subsequent rough and/or fine preparation with a drive head in accordance with the invention of the correct size. Here, a measurement tool 75 is advantageously suitable which will be described below. So far as the pre-preparation is effected without a remainder wall 74, the neighbouring tooth surface may be protected with a thin steel material strip and the relevant width of the pre-prepared cavity K up to the tooth 72 can be measured and a desired approximal safety spacing can be taken into account. The tool having the appropriate drive head 42a is schematically indicated in FIG. 17. With regard to its dimensions b, c and d, the drive head 42a is somewhat larger than the prepreparation so that the prepared cavity K corresponds with regard to its form and size, taking into consideration the play S arising, to the form and size of the working head 42a, so far as the drive head 42a enters into the tooth 71.

Figure 19:
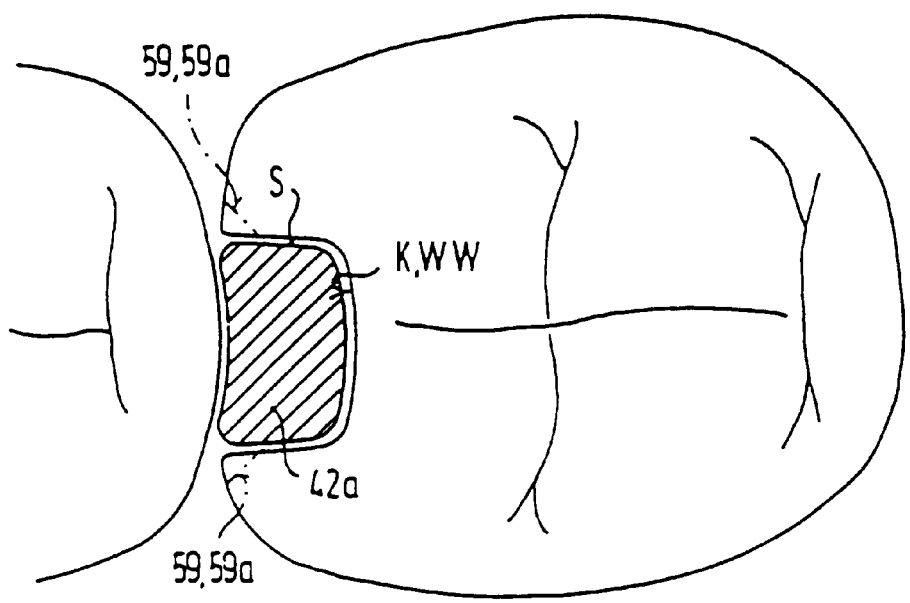
FIG. 19 the tooth, in a view from above, with a working head arranged in the cavity.
Figure 20:
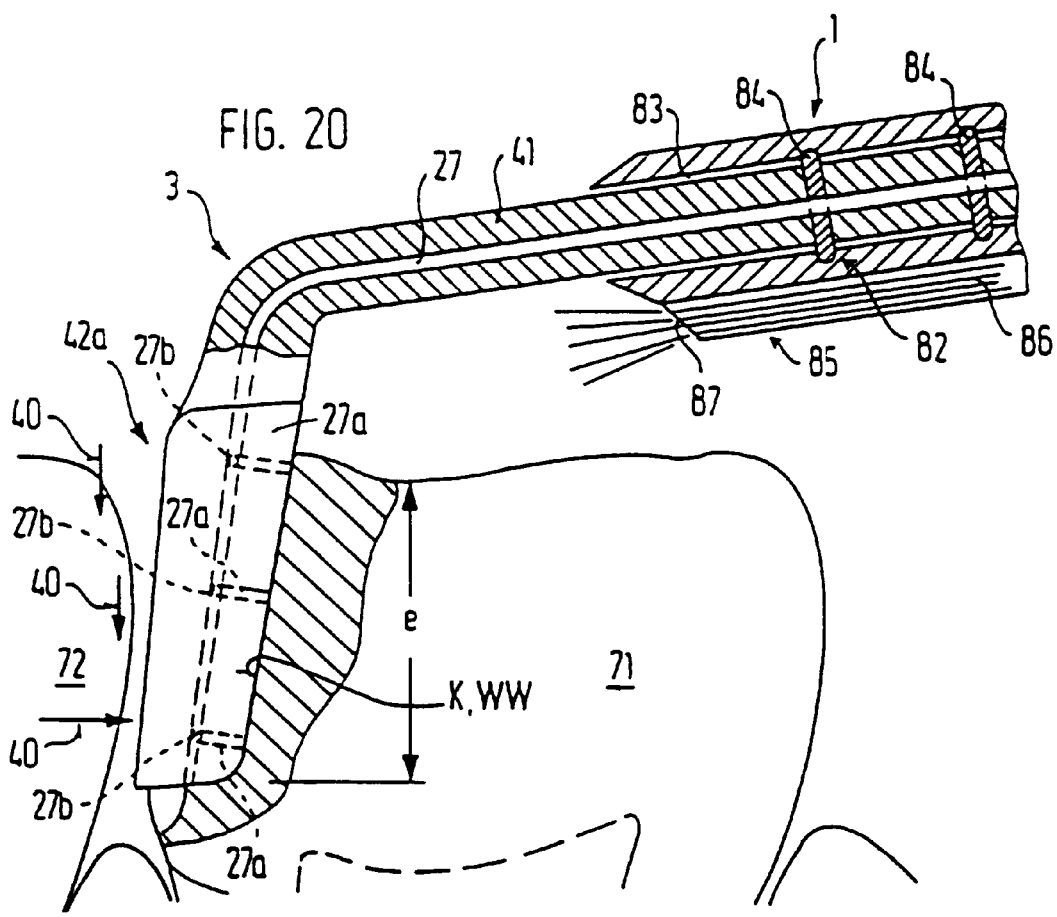
FIG. 20 the arrangement according to FIG. 19 in a modified configuration, in a side view, partially sectioned.

FIGS. 19 and 20 show the drive head 42a without divergent surfaces 59, which in the case of the present exemplary embodiment can be followed by working with working heads 42c, 42d. The carrying out of the fine preparation with and without divergent surfaces is dependent upon the later treatment technique.

The drive heads 42 to 42e may have channel branches 27a, 27b, 27c branching off from the common supply channel 25, which channel branches open at the working surfaces and in oscillation operation cool the working head and the tooth material, and wash away removed particles.

In FIG. 20, the grip sleeve 1 is furthermore formed with a schematically represented plug-in coupling 82, consisting of a plug-in hole 83 for insertion of the shaft 41 and at least one coupling element 84 which automatically latches upon insertion into coupling recesses of the shaft 41 and automatically un-latches upon pulling out. Further, the grip sleeve 1 has at its forward end an illuminating device 85 for illuminating the treatment site, preferably in the form of a light conductor 86, extending longitudinally on or in the grip sleeve 1, the light exit surface 87 of which is directed at the treatment site.

After, if appropriate repeated, measurement of the depth e of the cavity there is effected the selection of one of a plurality of available, pre-fabricated inserts 91, prepared according to the respective bonding system being used with dental material, taking into account the last used working head and if appropriate the depth e of the cavity K. After cleaning and if appropriate further conventional pre-treatment measures, and the application of a suitable bonding material 92 to the cavity walls KW, the insert 91 can be set in the cavity in accordance with FIGS. 21 and 22 and bonded in conventional manner by means of the bonding material 92 with the tooth 71. For the purposes of improving the exit of excess bonding material, release grooves 90 may be arranged in the contact surfaces of the insert 91, which release grooves preferably extend to the occlusal region.

The pre-fabricated insert 91 may be of metal or composite plastics or a translucent material such as e.g. glass, quartz or ceramics. The dimension e1 of the insert extending longitudinally of the tooth axis, may be differently dimensioned for various reasons. If, after the fixed emplacement of the insert 91, an occlusal building up on the insert 91, if appropriate also for further regions of the tooth 71, is intended then the amount e1 may be less than the depth e of the cavity K. Otherwise the amount e1 should be somewhat greater than the depth e so that the occlusal end region of the emplaced insert 91 can be adapted, with regard to dimensions and form, to a desired predetermined occlusal shape by removal of material before or after the fixing in place.

Since the insert 91 is matchingly pre-fabricated in the region enclosed by the cavity walls KW, an adaptation in this region is not needed. The approximal surface 91a of the insert is likewise pre-fabricated whereby its form and dimensions can be made ideal. With all configurations, the tool 42 and the insert 91 can have divergent surfaces 59 or bearing surfaces 59a, as is schematically illustrated in FIGS. 19 and 21.

Figure 21:
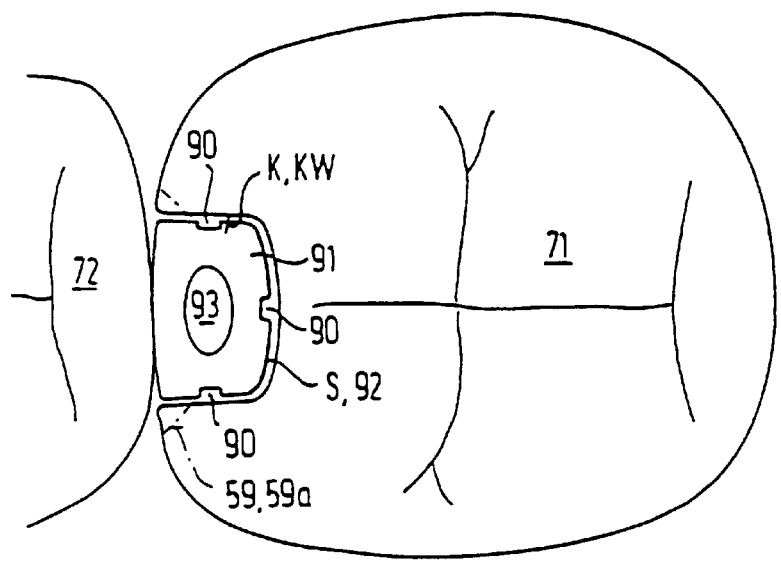
FIG. 21 the tooth, in a view from above, with an insert placed in the cavity.
Figure 22:
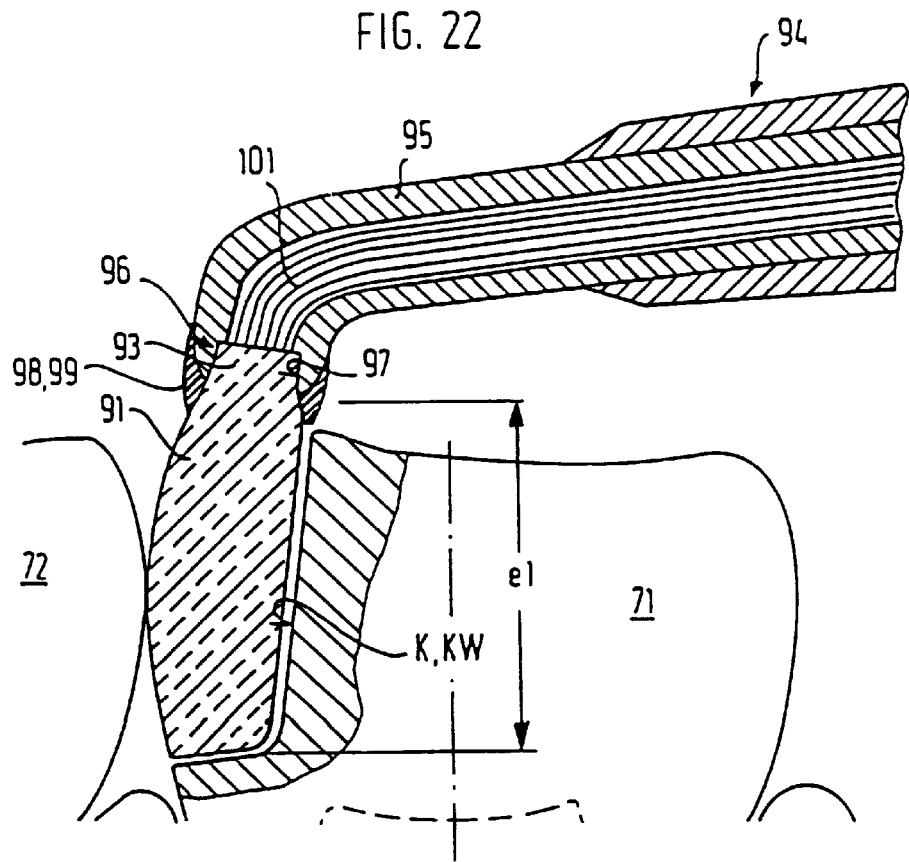
FIG. 22 the arrangement according to FIG. 21 in a side view, partially sectioned.

With the exemplary embodiment according to FIGS. 21 and 22, an insert 91 is employed which has at its occlusal end an application portion 93, of a particular cross-sectional form and size, which projects beyond the dept e of the cavity K, and which application portion is preferably formed integrally in the pre-fabrication. The application portion 93 makes possible the manipulation and working of the insert 91 with a particular handpiece 94 the forward region of which is illustrated in FIG. 22 in longitudinal section. This handpiece 94 has the form of a thin rod which has at its forward end a functional arm 95 with a lateral adaptor part 96 for the application portion 93. With the present configuration, the adaptor part 96 is formed by means of a matching receiving hole 97 for the adaption portion 93 and a clamping element 98 for holding the adaption portion 93 or insert 91 at the adaptor part 96. The clamping element 98 may be formed by means of one or two oppositely lying lips or an annular lip 99 of elastic material such as plastics or rubber or hard rubber. The clamping effect is achieved in that the opening bounded by the lip or lips 99 is in cross-section smaller than the adaption portion 93 so that in the inserted condition a clamping effect is present. Preferably, the functional arm 95 can be driven to oscillate by means of a drive in the handpiece 94 whereby the insert 91 can by forcibly emplaced by means of the transfer of vibrations.

Further, a functional arm 95 may have at its free end region a light generating device or a light conductor 101. With these means it is possible with an insert 91 of translucent material to direct light to the cavity walls KW from the light generation device or from the light conductor 101 through the application portion 93—or if such is not present—directly from above into the translucent insert 91 and thus to the cavity walls KW, in order to harden or cure a light or dual harden or bonding medium 92, e.g. a fine hybrid composite.

After curing, the application portion 93 is worked away with the removal of material, taking into consideration the required matching form.

Within the scope of the invention it is further advantageous to have available for each size or for the usual sizes a plurality of inserts 91 of different coloring, in order to be able to select the insert 91 not only with regard to its size but also its coloring and to adapt to given tooth colors.

Within the scope of the invention it is further possible and advantageous to mold or press an insert 91A at the available work station, whereby through mixing or selection of the molding or pressing material an appropriate color can be provided for the insert 91A. For this purpose there is provided in accordance with FIGS. 23 and 24 a casting mold 103 with two mold parts 104 in which there are present in the region of the dividing seam 105 at least one, preferably several, mold chambers 106 of shapes and sizes predetermined by the shapes and sizes of the available working heads. The mold parts 104 can be fastened against one another through suitable means, e.g. by means of screws. Further, there is provided at least one container with a plastic molding or pressing material for the molding/pressing of the insert 91A. If appropriate, a plurality of containers with molding/pressing materials of different colorings may be available (e.g. light hardening filling composite material's which after pressing into the negative mold in a closed system/chamber can thereafter be tempered with light and/or heat and/or pressure) so that by means of the selection of the container a particular color can be associated with the insert 91A. After selection of the particular size of the insert 91A, taking into consideration the size of the working head, the molding/pressing material is charged under pressure into the selected molding chamber 106 of corresponding size and shape which may be effected by means of an associated channel in the casting mold 103. After curing of the thus formed insert 91A, adapted to the size and shape of the working head used or to the cavity K, the insert can be emplaced in the associated cavity and further worked.

With the above-described measures, an application portion 93 in the sense described above can also be formed when the associated mold chamber or mold chambers 106 also have an application portion 93 of corresponding form.

It is also possible within the scope of the invention to form the application portion 93 by means of a pre-fabricated core 107 which consists of the application portion 93 and an anchoring section 108 and is so arranged in the associated mold chamber 106 before the molding that the anchoring portion 108 projects into the mold chamber 106 and can be formed around with the molding material. For receiving the core 107 in the mold form 103 corresponding recesses are provided into which the core with its application portion 93 can be emplaced.

Figure 18:
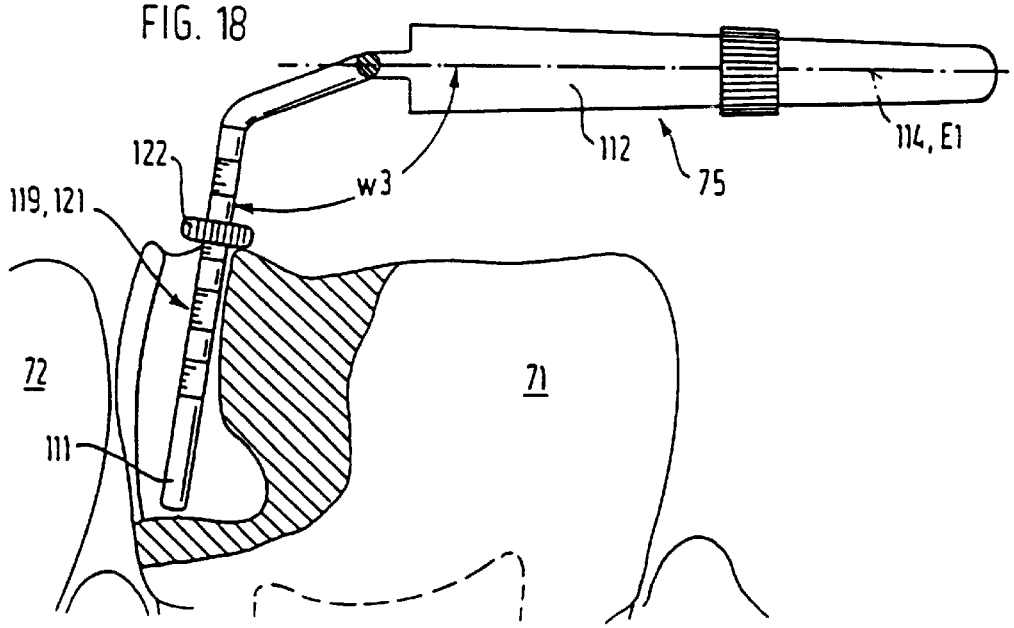
FIG. 18 the arrangement according to FIG. 17 in a side view, partly sectioned.

The measuring tool 75 has two measuring pins 111 which extend parallel to one another and have a length which is greater than the greatest depth $e$ of a cavity K. The cross-sectional size of the in particular round measuring pins 111 is preferably smaller than the smallest possible cross-sectional size of a cavity K, so that large and small cavities can be measured. The measuring pins 111 are each arranged on a measuring arm 112 which arms are guided so as to be movable towards one another and away from one another in a guide 113. Thereby, the measuring pins 111 extend from the measuring arms 112, seen in the direction of the longitudinal axis 114 of the measuring tool 75, approximately at right angles to the guide plane E1. Seen transversely to the longitudinal middle plane E2 of the measurement tool 75, the guide pins 112 enclose with the guide plane E1 or the measuring arms 112 an angle W3 of approximately 70 to 135 degrees, preferably approximately 90 to 110 degrees. In the present configuration, the guide 113 is formed by means of a joint 115 in which the two measuring arms 111 are connected with one another and which defines the guide plane E1 by means of the associated joint plane. With the present configuration, the joint 115 is arranged at the ends of the measuring arms 112 away from the measuring pins 111. Between the measuring arms 111 there is arranged a spring 116, in particular a compression spring, which biases the measuring arms 112 into their end positions, here into their spread-apart end position. Further, there is arranged between the measuring arms 111 a measuring device 117 having a scale 118, which makes possible a reading off of the respectively measured dimension of the cavitation. A second measuring device 119 is associated with one or with both measuring pins 111. This measuring device 119 also has a scale 121 on the associated measuring pin 111, by means of which the depth $e$ of the cavity K can be read off, as is illustrated in FIG. 18. It is also possible, preferably in combination with the scale 121, to arrange a clamping part, in particular a clamping ring 122, on the associated measuring pin 111, which is displaceable and thus—with the measuring pin 111 set on the floor of the cavity—is displaceable on to the occlusion surface of the tooth 71. In this way, either directly by means of comparison of the scale 121 with the occlusion surface or with the clamping ring 122, or by means of a measurement of the spacing of the clamping ring 122 from the free end of the measurement pin 111, the depth $e$ can be determined.

In the case of a first treatment of carious defects lying inwardly in the tooth, the opening of the tooth outer surface may be effected either directly with the oscillating instruments or after pre-preparation with rotating drills which are matched in terms of size, i.e. are smaller than the oscillating instruments.

Figure 27:
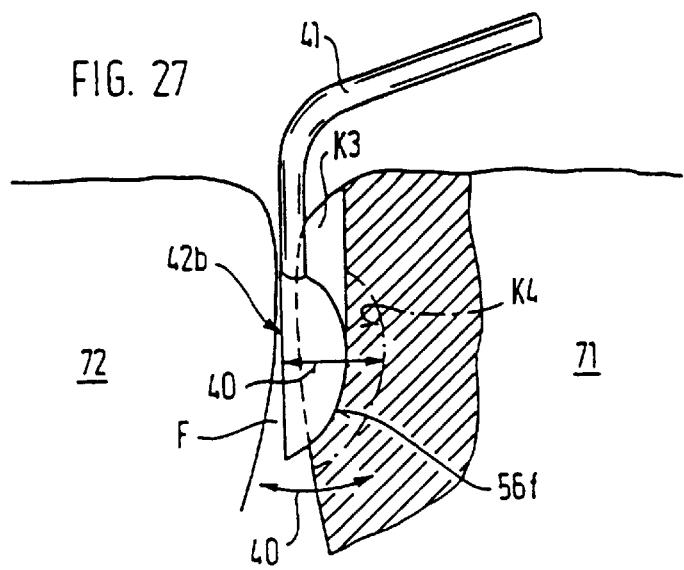
FIG. 27 a tooth and a cavity with a tool placed therein, in modified configurations, in a side view, partially sectioned.

With the configuration according to FIG. 27 a tool 42*b* in accordance with FIGS. 4 to 5, of pear or lentil shape, is used to treat an approximal primary carious defect. As is the case with the above-described exemplary embodiments, the tool 42*b* may be formed with or without neck surface 56*g*. With longitudinal or transversely oval extension of the caries to the approximal outer surface of the tooth 71 a relatively small cavity K3 can be configured with the working head 42*b*, from the buccal, from the lingual or from the occlusal side, whereby if appropriate pre-working with a smaller rotating tool may be effected. The working head 42*b* can thus be sunk in and guided to the approximal tooth enamel defect. The lateral abrasivity is sufficient for the removal of substance. Damage to the neighbouring tooth 72 is prevented by means of the free surface F. First, there arises an image of the working head 42*b* on the outer surface of the tooth 71. If the decalcification zones of the caries extend further laterally, the decalcification zone can be included in the preparation by means of a horizontal sinking in of the working head 42*b* or through a pivoting of the same in anti-clockwise direction (see the double arrows) whereby the schematically illustrated cavity K4 can be introduced. Thereafter, the working head 42*b* can be drawn back into the cavity K3 and then removed to the outside. By these means, the occlusal opening is reduced to a minimum. The treatment of the cavities can then be effected in a manner known per se.

Figure 28:
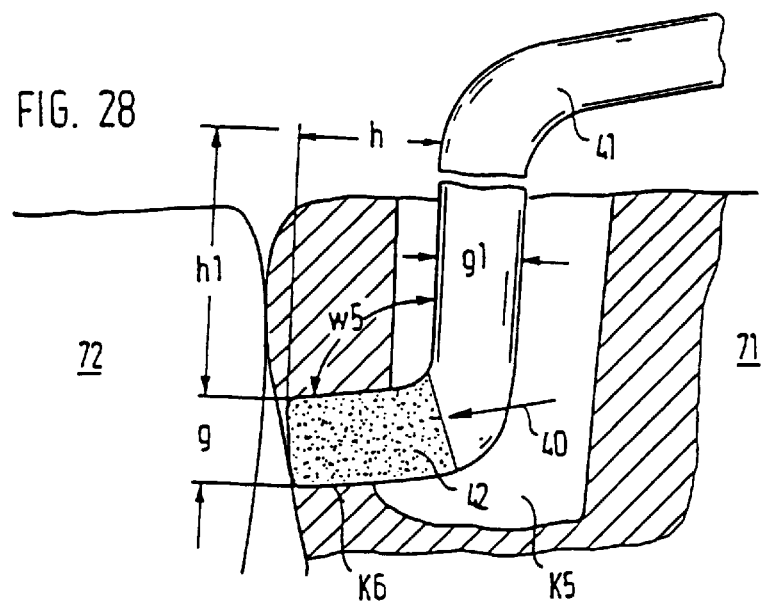
FIG. 28 a tooth and a cavity with a tool placed therein, in further modified configurations, partially sectioned.
Figure 28A:
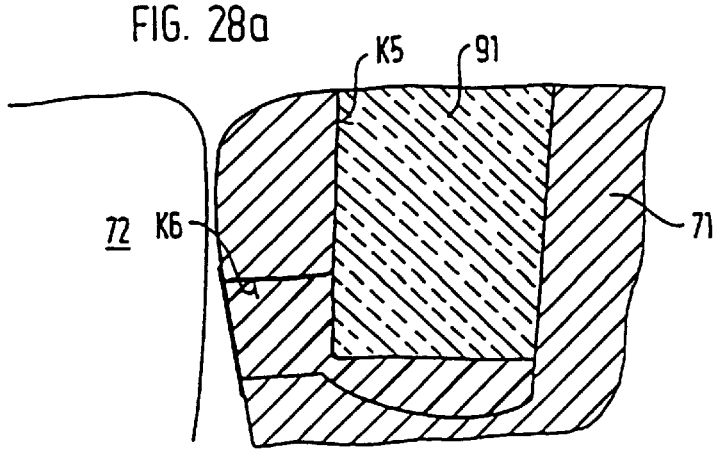
FIG. 28a the tooth according to FIG. 28 in the treated condition.

With the configurations according to FIGS. 28 and 28*a*, in which the same or similar parts or elements are likewise provided with the same reference signs, the repair of an in particular primary approximal carious defect is effected through an occlusal or also lateral or lingual or buccal cavity K5, so that a destruction of the tooth enamel in the region of the approximal tooth surface which has not been affected by the caries is avoided so far as possible. This measure is suitable in particular when the tooth 71 to be treated has already received an occlusal, lingual or buccal preparation, so that a cavity K5 already present or, if applicable to be made free, can be exploited for this cavity K6.

With this configuration, the tool 3 is formed with an angle-shape or a Z-shape, whereby the working head is formed by means of the free end limb of the angle or Z-shape. The cross-sectional form of the working head 42 may be circular or oval in vertical or horizontal direction. The angle $w5$ enclosed between the shaft 41 and the working head 42 is preferably a slightly obtuse angle and may be between approximately 90° and approximately 110°. The cross-sectional dimension $g$ of the working head 42 may be approximately 0.8 to 2 mm. For small cavities K6, the cross-sectional dimension $g$ is approximately 0.8 to 1.2 mm. Relative to this, the cross-sectional dimension $g1$ of the shaft 41, in particular round in cross-section, should be approximately the same or somewhat smaller. The length $h$ of the working head 42 may be approximately 1 to 3 mm, preferably 1.5 to 2 mm. The length $h1$ of the shaft section 41*a*—in the case of a Z-shape tool 33 the middle shaft section—should be so large that approximal defects can also be reached even in deeper regions of the tooth, so that one and the same tool 3 can be put to use for carious defects lying at different depths. Preferably, the length $h1$ is approximately 5 to 10 mm. The preferably obtuse angle between the shaft sections 41*a* and 41*b* may correspond to the configurations according to FIGS. 1 to 4*a* and is preferably approximately 90 to 120°. The cross-sectional size of the working head 42 may be slightly convergent towards its free end, in order to make more easy the withdrawal inwardly out of the cavity K6. Since, however, the cross-sectional size of the cavity K6 may preferably be made larger, the above-mentioned convergent shape of the working head 2 is not an absolute necessity. The working head is abrasive at its peripheral surface and its end surface.

The cross-sectional depth and size of the cavity K5 should be so large at the tool 3 can be readily introduced with the working head 42.

FIG. 28a shows the treated defect, whereby the cavities KS and K6 are able to be filled and thus treated with the same material or with different materials. For filling, materials which are applied in a plastic form, of medium viscosity, are suitable, e.g. composites and composite thermoplastics (Kompionomere). It is possible to work on the larger cavity K5 with a working head 42 which, in cross-section, has corners or is round, in accordance with FIGS. 1 to 1b, e.g. after a prior opening by means of a conventional rotating drill. It is also of advantage to provide the cavity K5 with an insert 91 the cross-sectional form and size of which are adapted, in the sense in accordance with the invention, to the cross-sectional form and size of the working head 42 (see e.g. FIGS. 1a and 1b).

Above-described tools can also be employed very advantageously for the removal of a furcation problem which arises in the case of paradontal bone atrophy at teeth with on or more roots and includes in the case of partially or completely opened furcations, contaminations, incidence of tartar and sources of bacterial infections. Such a furcation problem can be removed very well the tools 3 in accordance with the invention whereby in such cases in which the neighbouring surfaces should remain untreated, tools 3 having a free surface F can be employed, such as is the case e.g. in the approximal furcation region or in the furcation region of teeth with multiple roots.

FIGS. 29 to 36 show tool configurations which are advantageously suitable for the removal of furcation problems.

With the configuration according to FIGS. 29 to 31, the tool 3 consists of a connection part for connection with a schematically represented holder and drive part 128 of a handpiece, whereby the drive part 128 is oscillatingly driven in the longitudinal direction of the tool 3. Here, short oscillations may be involved which are generated by an oscillation source 2 or also longer to and fro movements may be involved such as is per se the case with handpieces for file tools for root canal treatment or the like.

With the present configuration, the connection part is formed by means of a sleeve-like clamping clasp in the form of a small tube 129 longitudinally slit by means of a slit 130, which can be plugged onto, and held thereon by means of clamping tension, a drive part of corresponding cross-sectional form, preferably cylindrical. From the clamping clasp 131 there extends a flat shaft 132 either straight or laterally offset forwardly, on the free end of which a working head 133 is arranged. The shaft 132 is elastically bendable laterally. Preferably, the tool 3 is formed as a stamped bending part from a one-piece blank, whereby the clamping clasp 134 is bent and the working head 133 is deep drawn, referably towards the side towards which the clamping clasp arms of the clamping clasp 131 are bent. The tool is preferably of a hard metal, in particular alloyed steel.

The convex outer surface 134 of the working head 133 is provided, in the sense already described, with a plurality of in particular point-like cutting edges which are arranged distributed and preferably consist of hard adherent grains, preferably of diamond, feldspar or ceramics, so that the working head 133 is abrasive at its working surface 134 and ensures a removal of material.

The head surface 134a and the side surfaces 134b of the convex working head 133 may be correspondingly abrasively formed. Also, the forward and rearward end faces 134c may be correspondingly abrasively formed. The head surface 134a is rounded at the transition into the other remaining working surface sections. The cross-sectional form of the working head 133 may thereby be flatly rounded or hemispherically rounded. The length $i$ of the tool 3 projecting from the connection part may be approximately 10 to 30 mm, in particular approximately 15 to 20 mm.

With the configuration according to FIGS. 32 and 33, the working head 133 has—preferably in its rearward end region—a transversely extending working edge 135 which may extend only in the region of the head surface 134a or also in the region of the side surfaces 134b and which may be stepped edge, which is of the material of the working head 42 or may be formed by means of a coating of the above-mentioned abrasive materials.

The length $k$ of the working head 42, diamondised on its working surfaces, may be approximately 1.5 to 5 mm, preferably about 2.5 mm. This applies also for the width $m$, which in the present exemplary embodiment is about 2 mm. With the present flat configuration of the working head 42, the thickness $n$ is about 0.5 to 2 mm, preferably about 0.75 mm. Insofar as the working head 133 is offset to the side relatively to the shaft 132, this amount of offset $o$ may be approximately 0.5 to 3 mm, in particular approximately 0.75 to 1 mm.

Figure 35:
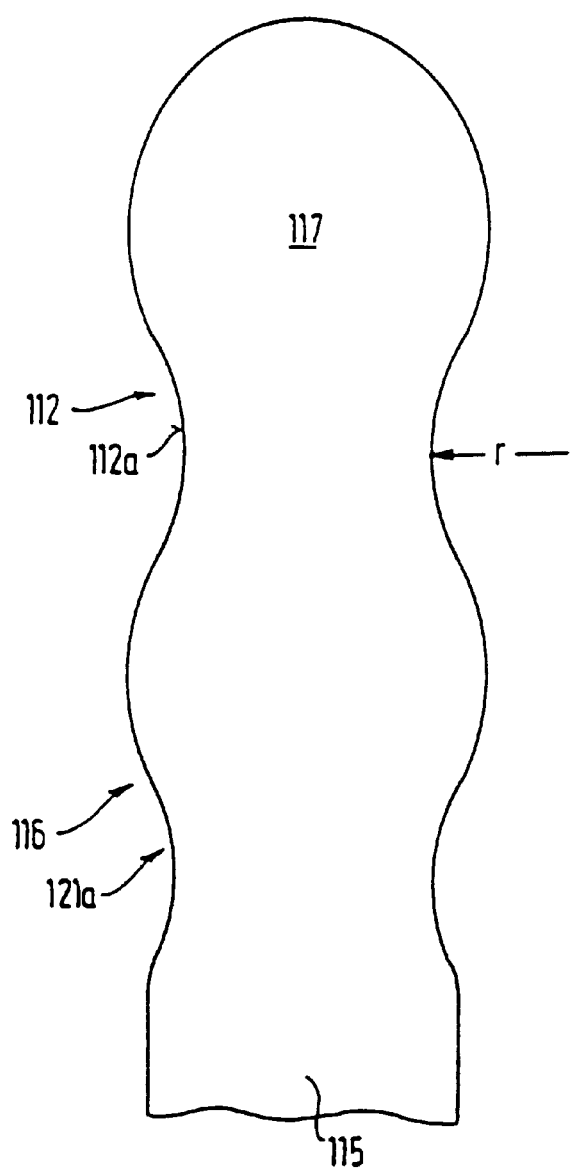
FIG. 35 a working head in a further modified configuration in a view from the front to an enlarged scale.
Figure 36:
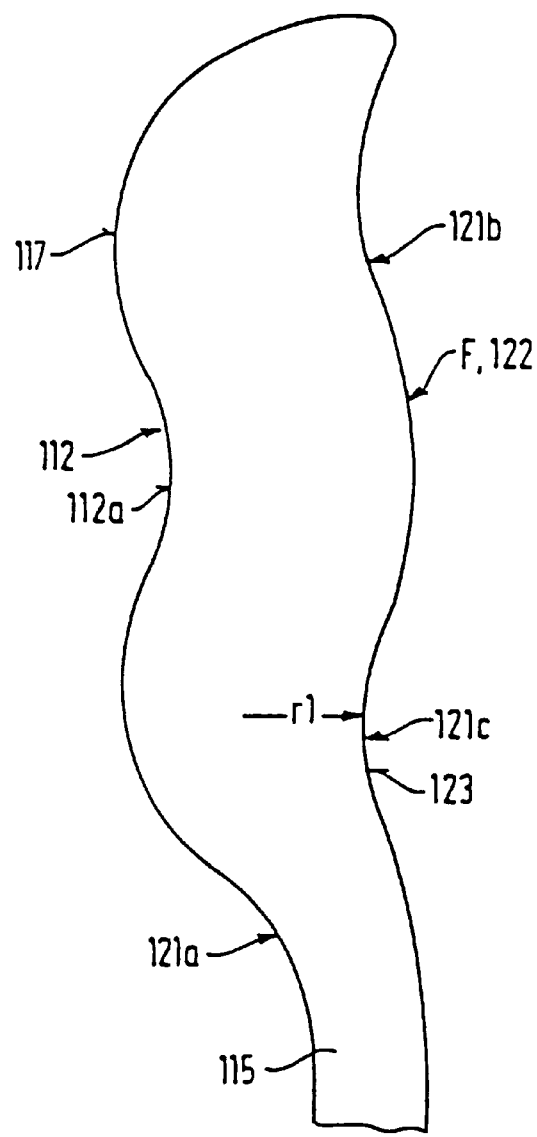
FIG. 36 the working head according to FIG. 36 in a side view.

With the configuration according to FIGS. 35 and 36, for which the same or similar parts are designated with the same references signs, the drive head 133 has at its lateral working surface at least one transversely extending waist 112, the waist surface 136a of which is rounded. The radius $r$ of this rounding is preferably somewhat larger than the radius of the tooth shape to be worked on. By these means, the abrasive treatment of a tooth surface, in particular in the root region of a furcation, is substantially simplified because the tooth surface parts before and behind roundings present can be better reached and the tool 3 need be moved less in order to reach these surface regions. As can be understood from FIG. 35, with a direction of view onto the working surface 134, the head end of the working head 133 is rounded, preferably hemispherically rounded, whereby this rounding transforms into the waist 136. Further, at an axial spacing from the waist, there is in the starting region of the working head 133 a "half" waist 136a which forms a cross-sectional tapering directed toward the shaft 132. This working head 133 can, in cross-section, be formed flat in accordance with FIGS. 32 to 34 or rounded, in particular half-rounded with flat reverse side or completely rounded, in particular circularly rounded. Thereby, the reverse side, visible in FIG. 36, may be a non-abrasive smooth free surface F or may be formed to be abrasive in the above-described sense as with the other head and side surfaces, 134a, 134b. As FIG. 36 likewise shows, with the present configuration the reverse surface 137 opposite to the head longitudinal surface 134a is wave-like with a snake shape or S-shape, whereby two further one-sided waists 136b, 136c are formed which are axially offset relative to the waist 136, so that the waist 136 lies opposite, at the reverse surface 137, a rounded protrusion. The rounding surfaces 138 of these waists 136b, 136c and the rounded protrusion therebetween may have the same or preferably a somewhat larger radius $r1$ than the radius $r$ of the waists 136, 136a, whereby—with an abrasive reverse surface 137—through selective use of the head longitudinal surface 134a or the reverse surface 137 an adaptation to tooth cross-sections of different sizes is possible.

The abrasive working surfaces of this working head 133 are preferably diamondised. The diamondisation is 40, 15, 2 to 4 µm.

The configuration of a working head 42 of the tool 3 shown in FIGS. 37 to 39 is a further development of the configuration according to FIGS. 2, 2a and 3, whereby the same or similar parts are provided with the same reference signs. This configuration differs from the above-described in the following details:

First it is to be explained that this working head 42 is, for the purpose of simpler representation, shown in a position in which it—in comparison with its real position in the mouth—is slightly tilted in the anti-clockwise direction, which is made more clear by means of the middle line indicated by V which is intended to represent the vertical, which extends parallel to the theoretical vertical middle axis of the tooth 71 to be treated. In the real position, the free surface F is located in an approximately vertical position, depending upon how the dentist positions the working head 42.

A first difference consist in that the working head 42—as seen in a view from above or the view from below according to FIG. 39—is curved in approximate adaptation to the peripheral form of the tooth 71, whereby a concavely curved front surface 56b is provided. This transforms with rounding into the side surfaces 56c which are adjoined by the divergent surfaces 59 at all three sides present (lateral and lower). The divergent surface section 56a, starting from the floor surface 56d, develops correspondingly curved, whereby this edge surface section of the cavity K is likewise approximately adapted to the curvature of a tooth outer surface. The reverse surface 56a is likewise correspondingly curved in principle. With the present configuration, the reverse surface 56a has a flat reverse surface part 56a1 which extends in the middle region of the working head 42 (see FIG. 38) over the whole height of the working head, but in the lateral regions—because of the curvature of the reverse surface 56a—extends only over part regions, as can be understood from FIG. 39. Through the concave curvature of the front or working surface 56b lesser tooth material is taken away from a tooth 71 to be prepared, which contributes to the stability of the tooth.

A further difference consist in that at least at the lower side of the working head 42—in the case of the present configuration also the side surfaces—there projects a narrow step 125 slightly downwardly or laterally, here by an amount p of approximately 0.2 to 05 mm, at which the divergent surfaces 59 end. The thickness g of the step 125 is approximately 0.1 to 0.4 mm preferably about 0.2 mm.

The working head 42 is suitably for working in (if appropriate after previous preliminary work with a rotating drilling tool) both for a cavity K for an inlay or insert 91 (see e.g. FIG. 21) and also for working in or final working (possibly after preliminary work with a rotating drilling tool) of a cavity K for a tooth crown according to FIG. 40. In the case of provision of a tooth crown it is advantageous to work in the cavity so far that the step 125 forms a gingival step 126. In the case of the preparation of a cavity K for an inlay or insert 91 this can be carried out with or without gingival step 126.

The width s of the drive head 42 or of the cavity K is to be determined in accordance with the corresponding width of the carious defect. The greater the width s is i.e. the greater is the region of the curvature, the greater is also the angle w6 enclosed by the lateral divergent surfaces 59. With wide working heads 42 or cavities K. the angle w6 may be (depending on the size of the angle w1) 90° and more, e.g. in the region of premolars. It is thus advantageous to provide or to store a plurality of working heads 42 of different width s in order to have available a suitable working head for normal treatments. This applies also to correspondingly associated inlays or inserts 91 with regard to their width and their lengths e1 to be determined or likewise provided in steps, which also applies for all other above-described configurations of the working heads 42.

The divergence of the working head 42, directed towards the free end thereof, of approximately 2 to 8°, in particular 4 to 6°, is made clearer in the case of the configuration according to FIGS. 37 to 39 by the angle w7. Also with this configuration there may be provided in the working head 42 a cooling channel 27 opening out at the front surface 56b or a plurality of cooling channel branches opening out at the working surface part.

What is claimed is:

1. A tooth filling system for preparing and filling a cavity which extends into the side of a tooth, said system comprising:
    a vibratable tool having abrasive front and side surfaces, said side surfaces extending back from said front surface at an angle of divergence, whereby, upon vibration of said tool against the side of a tooth, said tool forms a cavity having cross-sections of the same size and shape as corresponding cross-sections of said tool; and
    an insert comprising a solid body formed with a tooth adhering region defined by a lateral front surface and lateral side surfaces which extend back from said front surface to a free surface of said insert, said insert having cross-sections which correspond in size and shape to the size and shape of corresponding cross-sections of said tool.

2. A tooth filling system according to claim 1 wherein:
    the side surfaces of the insert are bearing surfaces for abutting cavity walls formed by said tool and which are convergent in a direction in which said front surface faces.

3. A tooth filling system according to claim 1 wherein:
    the side surfaces of the insert are flat surfaces which extend in a straight manner in a the direction in which said front surface faces.

4. An insert according to claim 1 wherein:
    said insert is one of several inserts which differ from one another in at least one of the dimensions of their cross-sectional shape, their and their dimension extending at a right angle thereto.

5. A tooth filling system according to claim 1 wherein:
    the insert is made of a material chosen from the group consisting of metal, plastic, composite plastic, light transparent material and glass ceramics.

6. A tooth filling system according to claim 1 wherein:
    said insert is an insert chosen from the group which consists of approximal, occlusal, incisal, buccal and lingual inserts and wherein a free side surface of said insert is pre-fabricated.

7. A tooth filling system according to claim 1 wherein:
    the insert includes an application portion in an occlusal portion portion thereof.

8. A tooth filling system according to claim 1 wherein:
    said insert is one of several inserts which have differing widths, and wherein the angle enclosed by the diverging surfaces of each insert is larger the larger the width of the insert.

9. A tooth filling system according to claim 1 wherein said abrasive side surfaces of said tool converge in their working direction.

10. A tooth filling system according to claim 1 wherein said lateral side surfaces of said insert are convergent in a direction toward said lateral front surface.

11. A method of repairing a tooth comprising the steps of:
forming a cavity in a tooth by causing a tool to be vibrated against a side of said tooth, said tool comprising a solid body and having abrasive front and side surfaces, said side surfaces extending back from said front surface at an angle of divergence, the cavity formed by said tool being characterized by an inner surface within said tooth corresponding to the front surface of said tool and side surfaces which extend from said front surface at an angle of divergence out to an outer surface of said tooth; and thereafter
placing into said cavity a preformed insert which has external dimensions corresponding to the internal dimensions of said cavity.

12. A method according to claim 11 wherein the step of forming a cavity comprises moving said tool in a working direction into said tooth to form tooth cavity walls which are convergent in the direction of working.

13. A method according to claim 11 wherein the step of forming a cavity includes the step of forming cavity walls with flat surfaces of said tool.

14. A method according to claim 11 including the step of providing an insert which is made of a material chosen from the group consisting of metal, plastic, composite plastic, light transparent material and glass ceramics.

15. A method according to claim 11 including the step of providing an insert from the group which consists of approximal, occlusal, incisal, buccal and lingual inserts and wherein the chosen insert is pre-fabricated.

16. A method according to claim 11 including the step of providing an insert comprises which has an application portion in an occlusal portion portion thereof, which application portion projects beyond the depth extent of a cavity into which the insert fits.

17. In combination, at least one vibratory abrasive tool for preparing cavities in teeth; and a group of inserts for filling said cavities, said inserts each comprising a solid prefabricated body which has a front surface and side surfaces extending back from said front surface, at least the rear portion of said side surfaces extending at an angle of divergence, said inserts being of similar configuration and having front surfaces of different widths and side surfaces whose angle of divergence is increased with increase width of their respective front surfaces.

* * * * *

UNITED STATES PATENT AND TRADEMARK OFFICE
CERTIFICATE OF CORRECTION

PATENT NO.     : 6,254,393 B1
DATED          : July 3, 2001
INVENTOR(S)    : Burkhard Hugo It is certified that error appears in the above-identified patent and that said Letters Patent is hereby corrected as shown below:

<u>Title page,</u>
Before Item [21], insert the following:

-- This patent issued as a divisional of a continued prosecution application filed under 37 CFR 1.53(d) and is subject to the twenty year patent term provisions of 35 U.S.C. 154(a)(2). --
Item [22], delete "Filed: Nov. 27, 1998" and insert the following:
  -- PCT Filed:     Nov. 3, 1995
[86] PCT No.:     PCT/EP95/04328
    § 371 Date:    Jul. 2, 1996
    § 102(e) Date:  Jul. 2, 1996

[87] PCT Pub. No.:  WO96/14024
    PCT Pub. Date:  May 17, 1996 --

Signed and Sealed this

Eighteenth Day of November, 2003

JAMES E. ROGAN
*Director of the United States Patent and Trademark Office*